US012616727B2

(12) United States Patent
Hughes

(10) Patent No.: US 12,616,727 B2
(45) Date of Patent: May 5, 2026

(54) COMPOSITIONS, SYSTEMS, AND METHODS FOR IMPROVING HEALTH

(71) Applicant: Unicity Properties, Inc., Provo, UT (US)

(72) Inventor: Stewart Hughes, Provo, UT (US)

(73) Assignee: UNICITY PROPERTIES, INC., Singapore (SG)

( * ) Notice: Subject to any disclaimer, the term of this patent is extended or adjusted under 35 U.S.C. 154(b) by 384 days.

(21) Appl. No.: 18/344,718

(22) Filed: Jun. 29, 2023

(65) Prior Publication Data

US 2024/0000875 A1     Jan. 4, 2024

Related U.S. Application Data

(60) Provisional application No. 63/358,031, filed on Jul. 1, 2022.

(51) Int. Cl.

| | |
|---|---|
| *A61K 36/185* | (2006.01) |
| *A23L 2/52* | (2006.01) |
| *A23L 33/00* | (2016.01) |
| *A23L 33/105* | (2016.01) |
| *A23L 33/125* | (2016.01) |
| *A23L 33/155* | (2016.01) |
| *A23L 33/16* | (2016.01) |
| *A23L 33/21* | (2016.01) |
| *A61K 31/07* | (2006.01) |
| *A61K 31/197* | (2006.01) |
| *A61K 31/222* | (2006.01) |
| *A61K 31/315* | (2006.01) |
| *A61K 31/355* | (2006.01) |
| *A61K 31/375* | (2006.01) |
| *A61K 31/4178* | (2006.01) |
| *A61K 31/4415* | (2006.01) |
| *A61K 31/455* | (2006.01) |
| *A61K 31/519* | (2006.01) |
| *A61K 31/522* | (2006.01) |
| *A61K 31/525* | (2006.01) |
| *A61K 31/702* | (2006.01) |
| *A61K 31/714* | (2006.01) |
| *A61K 31/716* | (2006.01) |
| *A61K 31/732* | (2006.01) |
| *A61K 31/736* | (2006.01) |
| *A61K 33/08* | (2006.01) |
| *A61K 33/10* | (2006.01) |
| *A61K 33/24* | (2019.01) |
| *A61K 36/899* | (2006.01) |
| *A61P 3/04* | (2006.01) |

(Continued)

(52) U.S. Cl.
CPC .............. *A61K 36/185* (2013.01); *A23L 2/52* (2013.01); *A23L 33/105* (2016.08); *A23L 33/125* (2016.08); *A23L 33/155* (2016.08);

*A23L 33/16* (2016.08); *A23L 33/21* (2016.08); *A23L 33/30* (2016.08); *A61K 31/07* (2013.01); *A61K 31/197* (2013.01); *A61K 31/222* (2013.01); *A61K 31/315* (2013.01); *A61K 31/355* (2013.01); *A61K 31/375* (2013.01); *A61K 31/4178* (2013.01); *A61K 31/4415* (2013.01); *A61K 31/455* (2013.01); *A61K 31/519* (2013.01); *A61K 31/522* (2013.01); *A61K 31/525* (2013.01); *A61K 31/702* (2013.01); *A61K 31/714* (2013.01); *A61K 31/716* (2013.01); *A61K 31/732* (2013.01); *A61K 31/736* (2013.01); *A61K 33/08* (2013.01); *A61K 33/10* (2013.01); *A61K 33/24* (2013.01); *A61K 36/899* (2013.01); *A61P 3/04* (2018.01); *A61P 3/06* (2018.01); *A61P 3/10* (2018.01)

(58) Field of Classification Search
CPC .... A61K 36/185; A61K 31/07; A61K 31/197; A61K 31/222; A61K 31/315; A61K 31/355; A61K 31/375; A61K 31/4178; A61K 31/4415; A61K 31/455; A61K 31/519; A61K 31/522; A61K 31/525; A61K 31/702; A61K 31/714; A61K 31/716; A61K 31/732; A61K 31/736; A61K 33/08; A61K 33/10; A61K 33/24; A23L 33/30; A23L 33/105; A23L 33/16; A23L 33/125; A23L 33/21; A23L 33/155; A23L 2/52; A61P 3/04; A61P 3/06; A61P 3/10

See application file for complete search history.

(56) References Cited

U.S. PATENT DOCUMENTS

| | | | |
|---|---|---|---|
| 2005/0130933 A1 | 6/2005 | Jacobs et al. | |
| 2006/0051435 A1* | 3/2006 | Udell ..................... | A23L 33/20 |
| | | | 424/725 |

(Continued)

FOREIGN PATENT DOCUMENTS

| | | | |
|---|---|---|---|
| KR | 101923603 | | 11/2018 |
| RU | 2260986 | * | 9/2005 |

OTHER PUBLICATIONS

International Search Report issued in application No. PCT/US2023/026623, mailed Oct. 4, 2023.

(Continued)

*Primary Examiner* — Shirley V Gembeh

(74) *Attorney, Agent, or Firm* — Knobbe, Martens, Olson & Bear, LLP

(57) ABSTRACT

Provided herein are product combinations, methods, kits, and compositions related to improving health and well-being in a subject. Methods of improving health and well-being may include ingesting a yerba mate supplement after waking, fasting for a fasting interval, and ingesting a fiber supplement before meal consumption.

21 Claims, 12 Drawing Sheets

(51) Int. Cl.
    *A61P 3/06*         (2006.01)
    *A61P 3/10*         (2006.01)

(56)                 References Cited

U.S. PATENT DOCUMENTS

| | | | |
|---|---|---|---|
| 2011/0003021 A1 | 1/2011 | Halford et al. | |
| 2011/0189319 A1* | 8/2011 | Leitman | A61K 36/53 |
| | | | 426/2 |
| 2016/0113985 A1* | 4/2016 | Halford | A23L 33/15 |
| | | | 424/48 |
| 2018/0027860 A1 | 2/2018 | Halford et al. | |
| 2021/0290722 A1* | 9/2021 | Do | A61K 31/205 |

OTHER PUBLICATIONS

Sirtori et al., "Functional foods for dyslipidaemia and cardiovascular risk prevention", Nutrition Research Reviews, vol. 22, No. 2 ., Dec. 1, 2009 (Dec. 1, 2009), pp. 244-261, XP009144263.

* cited by examiner

COMPOSITIONS, SYSTEMS, AND METHODS FOR IMPROVING HEALTH

INCORPORATION BY REFERENCE

This application claims the benefit of U.S. Provisional Application No. 63/358,031, filed Jul. 1, 2022. The aforementioned application is incorporated by reference herein in its entirety.

FIELD

The present disclosure generally relates to product combinations, methods, kits, and compositions for improving health and well-being using a yerba mate supplement and a fiber supplement, and to methods, kits, and compositions for improving health and well-being by fasting for a fasting interval in combination with the compositions and product combinations described herein.

BACKGROUND

An epidemic of obesity and related cardiometabolic diseases, driven by poor diet and sedentary lifestyle, is spreading rapidly worldwide. A diet rich in dietary fiber can lower blood cholesterol levels and better manage blood glucose levels. In addition, high-fiber foods tend to provide better satiety, which aids in reducing calorie consumption.

Yerba mate, or *Ilex paraguariensis*, is one of the most commercialized medicinal plants of South America. It grows naturally and is cultivated in Argentina, Uruguay, Brazil, and Paraguay. The component parts of this plant are used to prepare a tea-like beverage (Croge et al., 2020). Yerba mate also has a long history of use worldwide. In Europe it is used for weight loss, physical and mental fatigue, nervous depression, rheumatic pains, and psychogenic- and fatigue-related headaches. In Germany, it has become popular as a weight-loss aid. Yerba mate is the subject of a German monograph, which lists its approved uses for mental and physical fatigue, and describes it as having analeptic, diuretic, positively inotropic, positively chronotropic, glycogenolytic, and lipolytic effects. In France, yerba mate is approved for the treatment of asthenia (weakness or lack of energy), as an aid in weight-loss programs, and to increase the renal excretion of water. It also appears in the British Herbal Pharmacopoeia (1996), with indications for the treatment of fatigue, weight loss, and headaches. In the U.S., yerba mate was recommended for arthritis, headache, hemorrhoids, fluid retention, obesity, fatigue, stress, constipation, allergies, and hay fever, and is used to cleanse the blood, tone the nervous system, retard aging, stimulate the mind, control the appetite, stimulate the production of cortisone, and is believed to enhance the healing powers of other herbs. Yerba mate is also cultivated in India, and the Indian Ayurvedic Pharmacopoeia lists maté for the treatment of psychogenic headaches, nervous depression, fatigue, and rheumatic pains (Heck & De Mejia, 2007).

The primary known bio-active chemical constituents of yerba mate include xanthine alkaloids, chlorogenic acids, and mate saponins. Xanthine alkaloids include, for example, caffeine (1,3,7-trimethylxanthine), theobromine (3,7-dimethylxanthine), and theophylline (1,3-dimethylxanthine), and analogues or derivatives thereof. Chlorogenic acids include, for example, caffeic acid and tannins, and analogues or derivatives thereof (Oellig et al., 2018). The content of yerba mate leaf has been assayed and reported to contain between caffeine by weight, 0.3%-0.9% theobromine by weight, theophylline in relatively minor amounts, saponins, and 10% caffeic acid derivatives (chlorogenic acid, caffeic acid, 3,4-dicaffoylquinic acid, 3,5-dicaffoylquinic acid and 4,5-dicaffoylquinic acid) (Matei et al., 2016). Other chemicals found in yerba mate include alpha-amyrin, alpha-terpineol, arachidic acid, beta-amyrin, butyric acid, 5-o-caffeoylquinic acid, calcium, carotene, choline, chlorophyll, cyanidin-3-o-xylosyl-glucoside, cyanidin-3-glucoside, essential oil, eugenol, geraniol, geranyl acetone, guayacan b, indole, inositol, ionone, iso-butyric acid, iso-caproic acid, iso-chlorogenic acid, iso-valeric acid, kaempferol, lauric acid, levulose, linalool, linoleic acid, maté saponins, neochlorogenic acid, nerolidol, nicotinic acid, nudicaucin c, octan-1-ol, octanoic acid, oleic acid, palmitic acid, palmitoleic acid, pyridoxine, quercetin, raffinose, safrole, stearic acid, tannins, theobromine, theophylline, trigonelline, and ursolic acid. In addition, 7%-14% of tannins were also reported in yerba mate leaf material (Bastos et al., 2007; Bojić et al., 2013; Burris et al., 2012; Chandrasekara & Shahidi, 2018; Chianese et al., 2019; Ferreira Cuelho et al., 2015; Frizon et al., 2018; Isolabella et al., 2010; Junior & Morand, 2016; Puangpraphant, 2012; Riachi et al., 2018; Souza et al., 2015).

Theobromine is used as a vasodilator, a diuretic, and a heart stimulator. Theobromine is recognized as an antagonist of the adenosine receptor, similar to caffeine, and an inhibitor of phosphodiesterase, and may be helpful in the management of fatigue and orthostatic hypotension.

SUMMARY

The present disclosure generally relates to product combinations, methods, kits, and compositions for improving health and well-being using a yerba mate supplement and a fiber supplement. In some embodiments, the methods include fasting during a fasting interval, in combination with the product combinations and compositions described herein.

Some embodiments provided herein relate to product combinations for improving health and well-being in a subject. In some embodiments, the product combinations include: a yerba mate supplement including at least 20% total chlorogenic acids, at least 0.3% theobromine, and 1-6% caffeine; and a fiber supplement including at least 3.5 g soluble fiber and 250-1000 mg phytosterols.

In some embodiments, the soluble fiber includes guar gum, locust bean gum, citrus pectin, oat fiber, beta-glucans, or gum arabic. In some embodiments, the fiber supplement further includes vitamin A, vitamin C, vitamin E, thiamin, riboflavin, niacinamide, pyridoxine HCl, folic acid, cyanocobalamin, biotin, calcium carbonate, zinc gluconate, chromium, a polyphenol blend, magnesium oxide, pantothenic acid, or short-chain fructo-oligosaccharides. In some embodiments, the yerba mate supplement is formulated as a powder or a drink. In some embodiments, the fiber supplement is formulated as a powder or a drink. In some embodiments, the yerba mate supplement and the fiber supplement are formulated for oral ingestion. In some embodiments, the yerba mate supplement and the fiber supplement are packaged separately. In some embodiments, the yerba mate supplement and the fiber supplement are formulated for ingestion at different time intervals. In some embodiments, the yerba mate supplement and the fiber supplement provide a synergistic effect when ingested separately. In some embodiments, the yerba mate supplement is formulated for ingestion at least once daily. In some embodiments, the fiber supplement is formulated for ingestion at least twice daily.

In some embodiments, the yerba mate supplement includes at least 600 mg of total chlorogenic acids. In some embodiments, the yerba mate supplement includes at least 9 mg of theobromine. In some embodiments, the yerba mate supplement includes at least 60 mg caffeine. In some embodiments, the yerba mate supplement includes about 600 mg of total chlorogenic acids, about 9 mg of theobromine, and about 120 mg of caffeine.

In another aspect, some embodiments provided herein relate to methods for improving health and well-being in a subject. In some embodiments, the methods include fasting during a fasting interval; ingesting a yerba mate supplement during the fasting interval; and ingesting a fiber supplement following the fasting interval.

In some embodiments, the fasting interval is for a period ranging from about 12 to about 18 hours. In some embodiments, the yerba mate supplement includes at least 600 mg of total chlorogenic acids. In some embodiments, the yerba mate supplement includes at least 9 mg of theobromine. In some embodiments, the yerba mate supplement includes 60-180 mg of caffeine. In some embodiments, the method further includes mixing the fiber supplement with liquid. In some embodiments, the liquid is water. In some embodiments, the liquid is tea. In some embodiments, the liquid is electrolyte solution. In some embodiments, the liquid is in an amount of at least 240 mL. In some embodiments, the amount of liquid is in a range from about 400 to about 800 mL. In some embodiments, the method further includes mixing the yerba mate supplement with liquid. In some embodiments, the fiber supplement is ingested prior to a first meal. In some embodiments, the fiber supplement is ingested about 1 to about minutes prior to the first meal, such as about 1, 2, 3, 4, 5, 6, 7, 8, 9, 10, 15, 20, 25, 30, 35, 45, 50, 55, or 60 minutes or within a time frame defined by any two of the aforementioned values, prior to the first meal. In some embodiments, the method further includes ingesting the fiber supplement before a second meal. In some embodiments, the fiber supplement is ingested about 1 to about 60 minutes prior to the second meal, such as about 1, 2, 3, 4, 5, 6, 7, 8, 9, 10, 20, 25, 30, 35, 40, 45, 50, 55, or 60 minutes or within a time frame defined by any two of the aforementioned values, prior to the second meal.

In another aspect, some embodiments provided herein relate to a kit. In some embodiments, the kit includes: a first composition including a yerba mate supplement including at least 600 mg total chlorogenic acids, at least 9 mg theobromine, and 60-180 mg caffeine; and a second composition including a fiber supplement including at least 3.5 g soluble fiber and 250-1000 mg phytosterols.

In some embodiments, the soluble fiber includes guar gum, locust bean gum, citrus pectin, oat fiber, beta-glucans, or gum arabic. In some embodiments, the fiber supplement further includes vitamin A, vitamin C, vitamin E, thiamin, riboflavin, niacinamide, pyridoxine HCl, folic acid, cyanocobalamin, biotin, calcium carbonate, zinc gluconate, chromium, a polyphenol blend, magnesium oxide, pantothenic acid, or short-chain fructo-oligosaccharides. In some embodiments, the yerba mate supplement is formulated as a powder or a drink. In some embodiments, the fiber supplement is formulated as a powder or a drink. In some embodiments, the yerba mate supplement and the fiber supplement are formulated for oral ingestion. In some embodiments, the yerba mate supplement and the fiber supplement are packaged separately within the kit. In some embodiments, the yerba mate supplement and the fiber supplement are formulated for ingestion at different time intervals. In some embodiments, the yerba mate supplement and the fiber supplement have a synergistic effect when ingested separately. In some embodiments, the yerba mate supplement is formulated for ingestion at least once daily. In some embodiments, the fiber supplement is formulated for ingestion at least twice daily. In some embodiments, the yerba mate supplement includes at least 600 mg of total chlorogenic acids. In some embodiments, the yerba mate supplement includes at least 9 mg of theobromine. In some embodiments, the yerba mate supplement includes 60-180 mg caffeine. In some embodiments, the kit further includes an electronic system to track intake of the yerba mate supplement or the fiber supplement. In some embodiments, the kit further includes an electronic system to track a fasting interval.

In another aspect, some embodiments provided herein relate to compositions for use in improving health and well-being. In some embodiments, the composition is for ingestion. In some embodiments, the compositions include: a yerba mate supplement including at least 20% total chlorogenic acids, at least 0.3% theobromine, and 1-6% caffeine; and a fiber supplement including at least 3.5 g soluble fiber and 250-1000 mg phytosterols.

In some embodiments, the soluble fiber includes guar gum, locust bean gum, citrus pectin, oat fiber, beta-glucans, or gum arabic. In some embodiments, the fiber supplement further includes vitamin A, vitamin C, vitamin E, thiamin, riboflavin, niacinamide, pyridoxine HCl, folic acid, cyanocobalamin, biotin, calcium carbonate, zinc gluconate, chromium, a polyphenol blend, magnesium oxide, pantothenic acid, or short-chain fructo-oligosaccharides. In some embodiments, the yerba mate supplement is formulated as a powder or a drink. In some embodiments, the fiber supplement is formulated as a powder or a drink. In some embodiments, the yerba mate supplement and the fiber supplement are formulated for oral ingestion. In some embodiments, the yerba mate supplement and the fiber supplement are packaged separately. In some embodiments, the yerba mate supplement and the fiber supplement are formulated for ingestion at different time intervals. In some embodiments, the yerba mate supplement and the fiber supplement provide a synergistic effect when ingested separately. In some embodiments, the yerba mate supplement is formulated for ingestion at least once daily. In some embodiments, the fiber supplement is formulated for ingestion at least twice daily. In some embodiments, the yerba mate supplement includes at least 600 mg of total chlorogenic acids. In some embodiments, the yerba mate supplement includes at least 9 mg of theobromine. In some embodiments, the yerba mate supplement includes at least 60 mg caffeine. In some embodiments, the yerba mate supplement includes about 600 mg of total chlorogenic acids, about 9 mg of theobromine, and about 120 mg of caffeine. In some embodiments, improving health and well-being includes improving blood lipid levels, reducing body weight, reducing fasting blood sugar levels, increasing feelings of positive experiences, and/or decreasing feelings of negative experiences.

BRIEF DESCRIPTION OF THE DRAWINGS

The foregoing and other features of the present disclosure will become more fully apparent from the following description, taken in conjunction with the accompanying drawings. Understanding that these drawings depict only some embodiments in accordance with the disclosure and are therefore, not to be considered limiting of its scope, the disclosure will be described with additional specificity and detail through use of the accompanying drawings.

5

Figure 1:
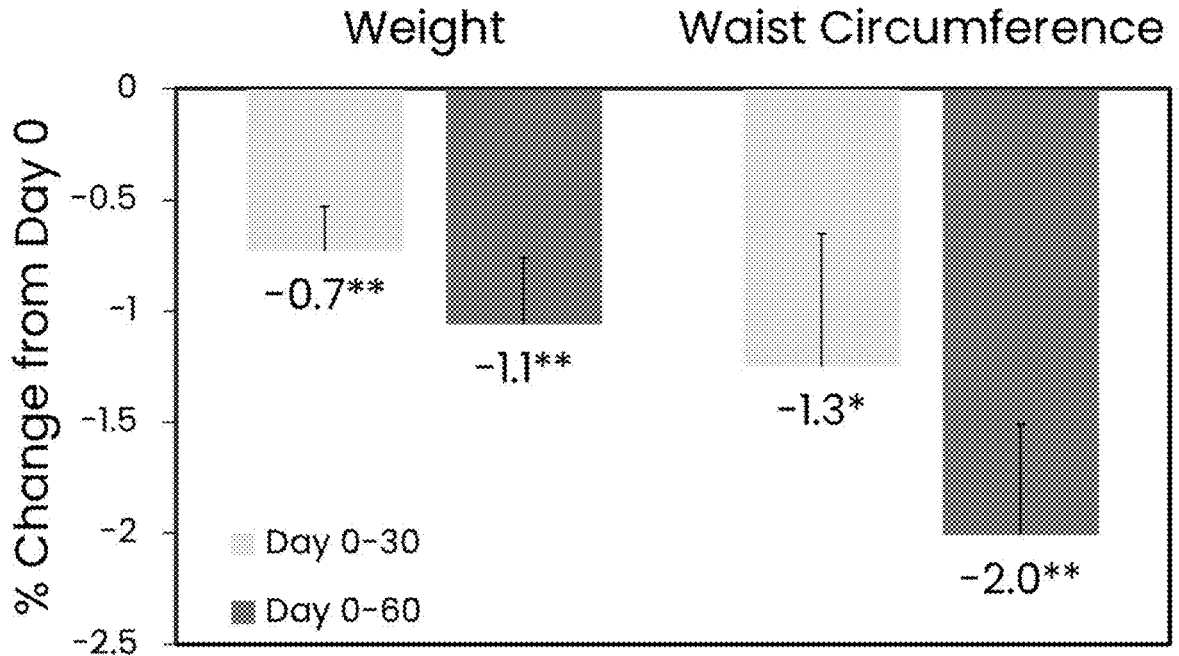

FIG. 1 illustrates a bar graph depicting an embodiment showing percent change in body weight and waist circumference of participants.

Figure 2:
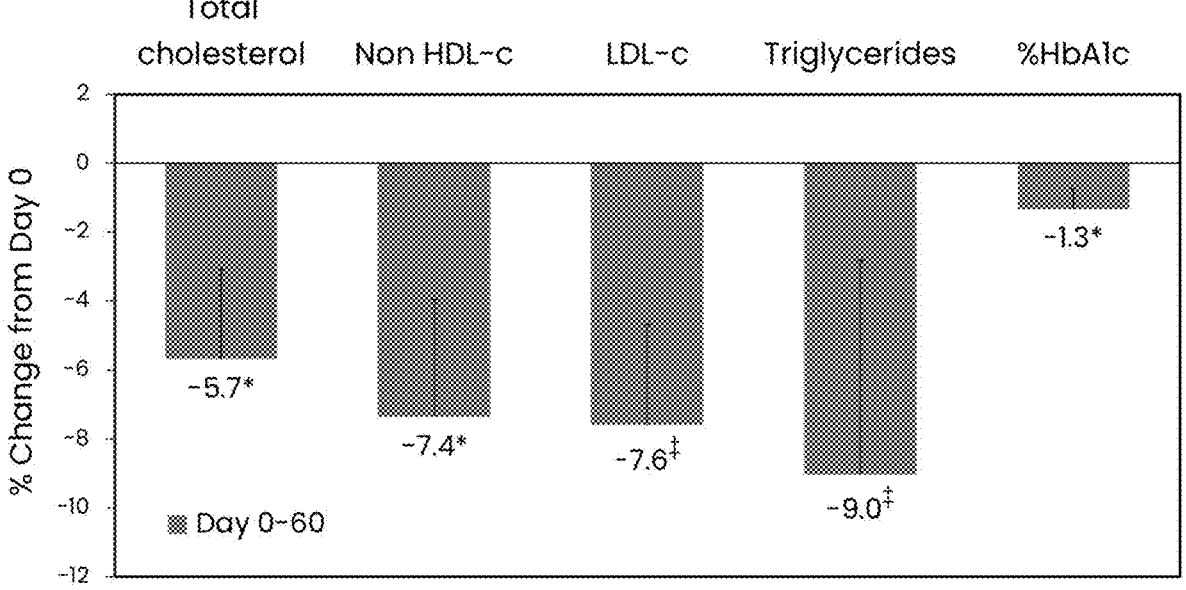

FIG. 2 illustrates a bar graph depicting an embodiment showing percent change from baseline to Day 60 in lipid and glucose biomarkers.

Figure 3:
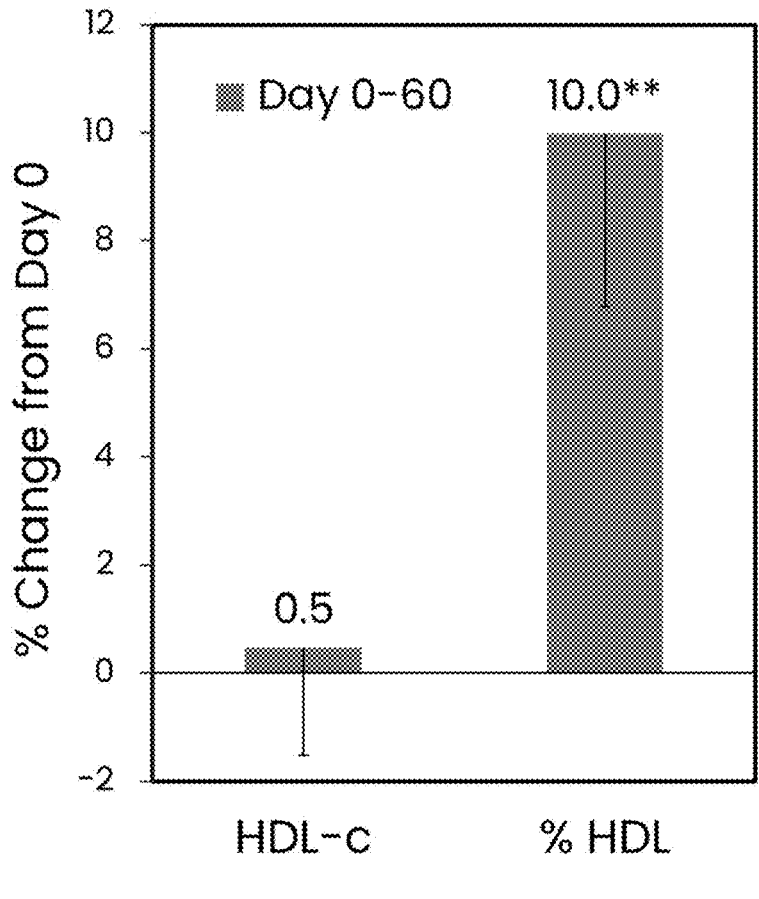

FIG. 3 illustrates a bar graph depicting an embodiment showing percent change from baseline to Day 60 in HDL cholesterol and % HDL.

Figure 4:
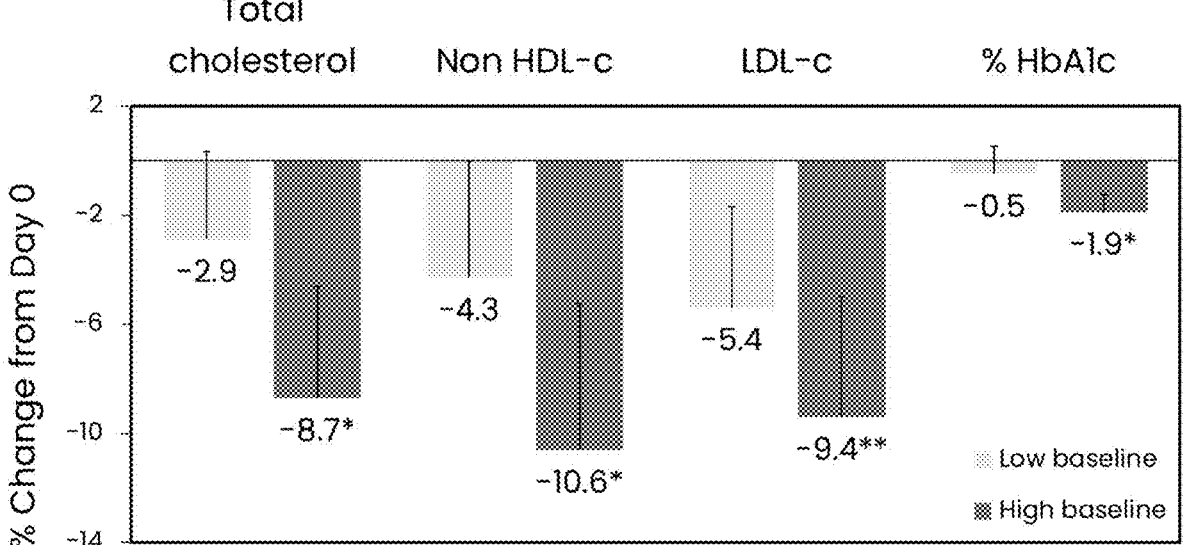

FIG. 4 illustrates a bar graph depicting an embodiment showing stratification of participants with Low vs High baseline non-HDL cholesterol.

Figure 5:
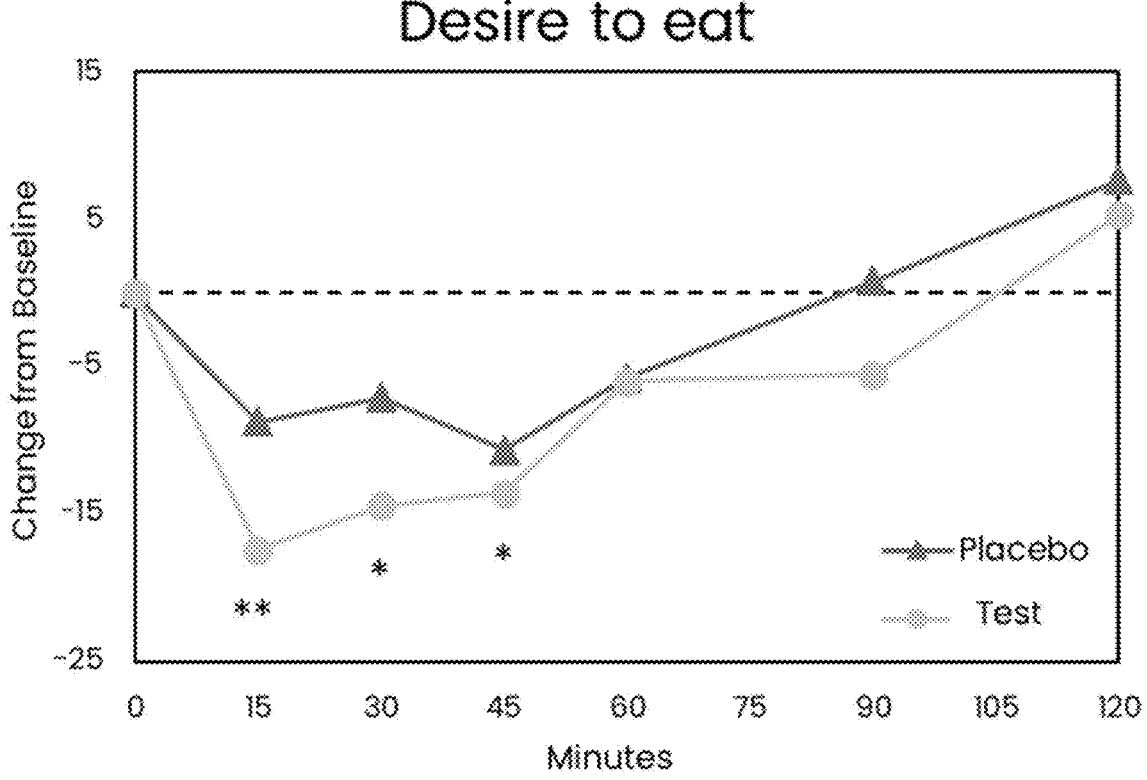

FIG. 5 illustrates a line graph depicting an embodiment showing lower desire to eat after consuming a yerba mate supplement.

Figure 6:
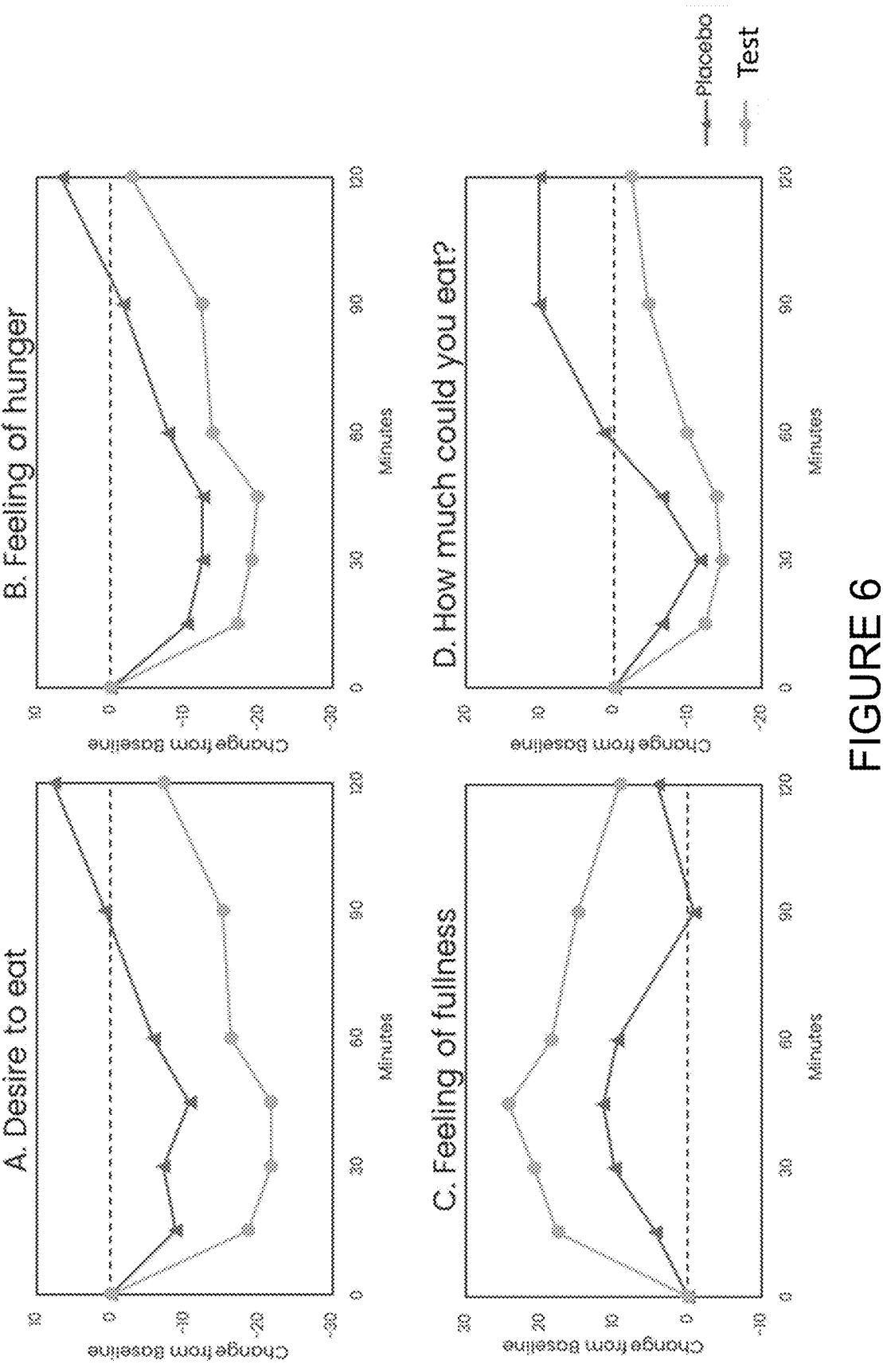

FIG. 6 depicts panels A-D and illustrates an embodiment of line graphs depicting desire to eat, feeling of hunger, feeling of fulness, and how much one could eat when participants consumed placebo (n=9) or a yerba mate supplement (test, n=26).

Figure 7:
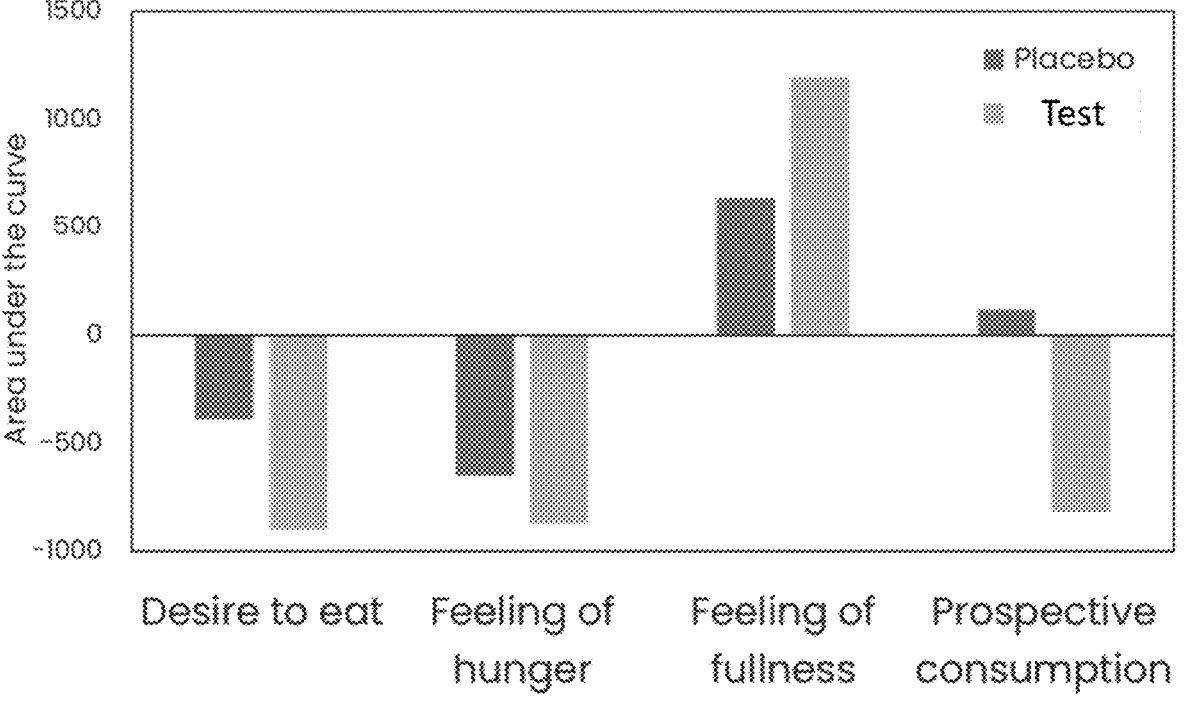

FIG. 7 illustrates a bar graph depicting an embodiment of paired within-subject comparisons (N=9) of AUC VAS appetite responses to yerba mate supplement versus Placebo.

Figure 8:
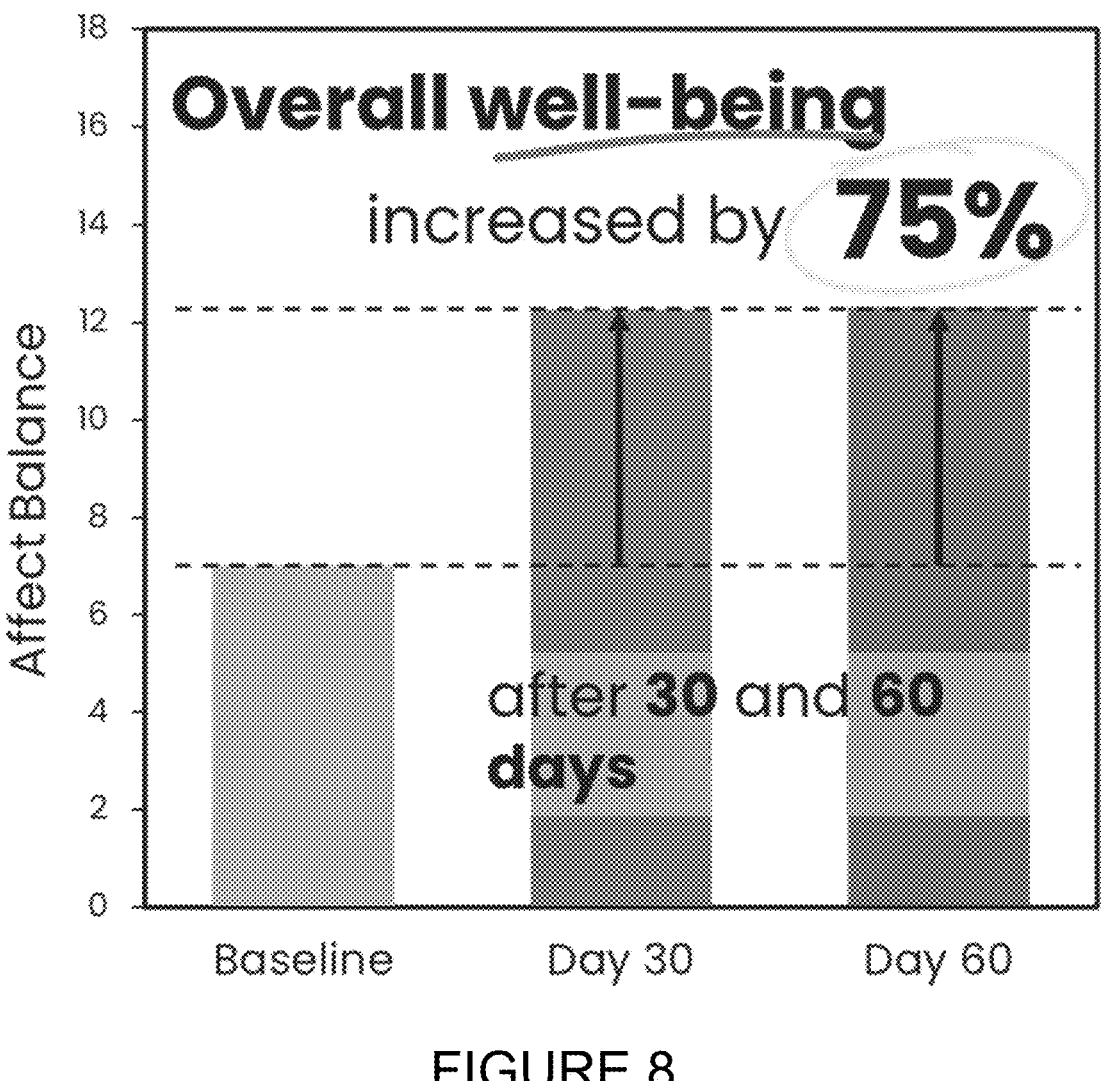

FIG. 8 illustrates a bar graph depicting an embodiment of improvements in well-being measured by SPANE (Scale of Positive and Negative Experiences) after 30 and 60 days of treatment with a method described herein.

Figure 9:
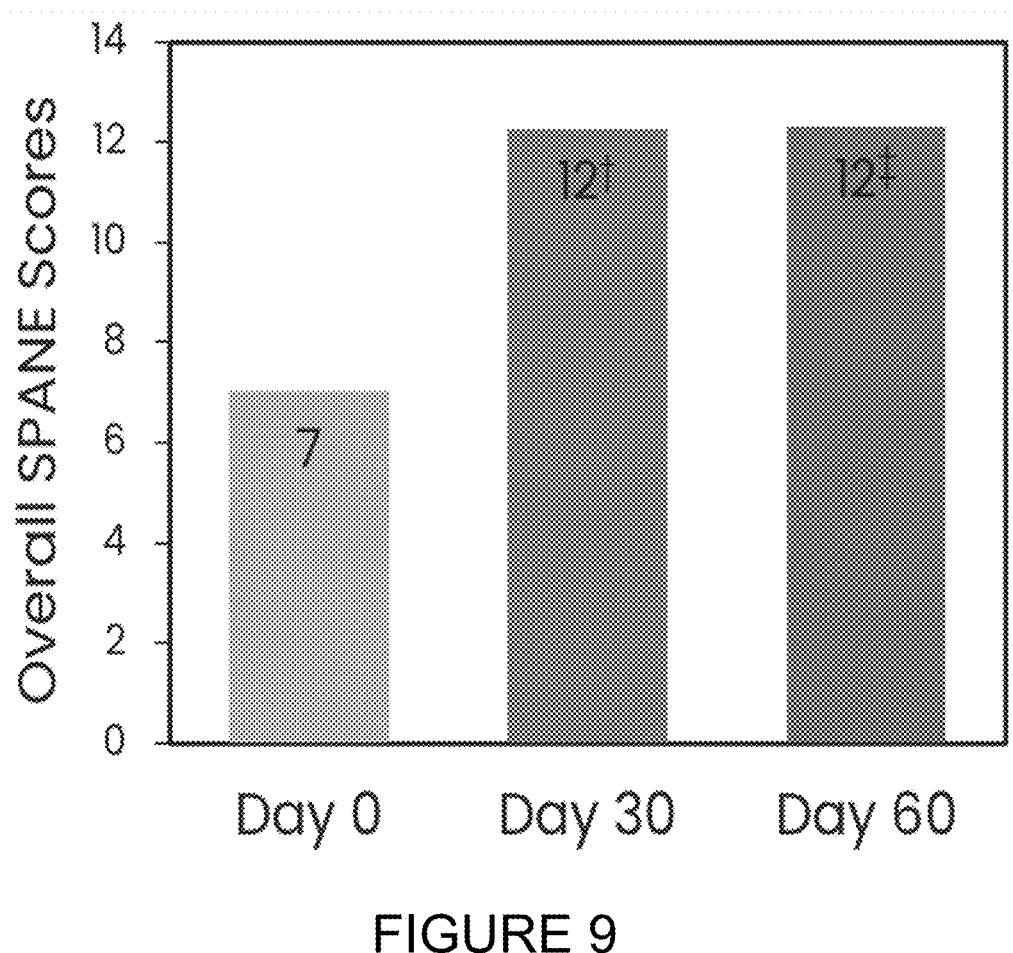

FIG. 9 illustrates a bar graph depicting an embodiment showing SPANE score (overall well-being) at Days 30 & 60, which significantly increased from Day 0.

Figure 10:
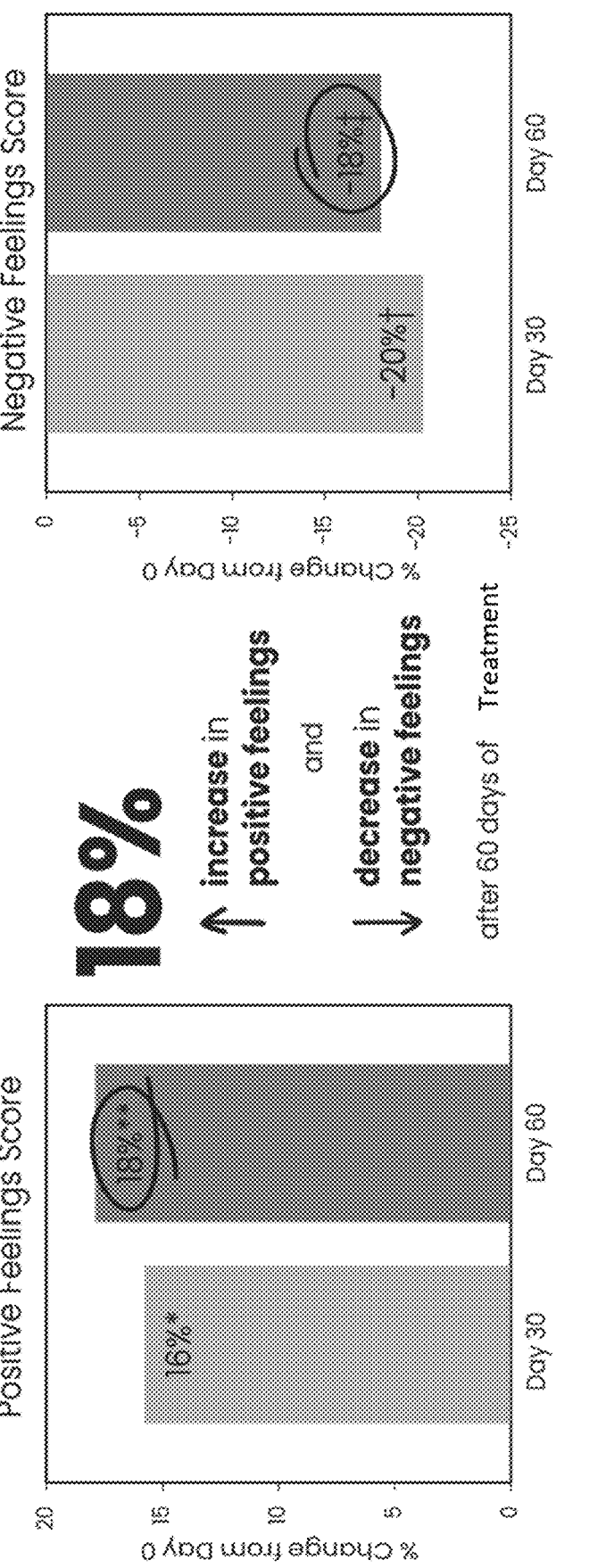

FIG. 10 illustrates a bar graph depicting an embodiment of changes in positive and negative feelings SPANE scores over 30 and 60 days of treatment.

Figure 11:
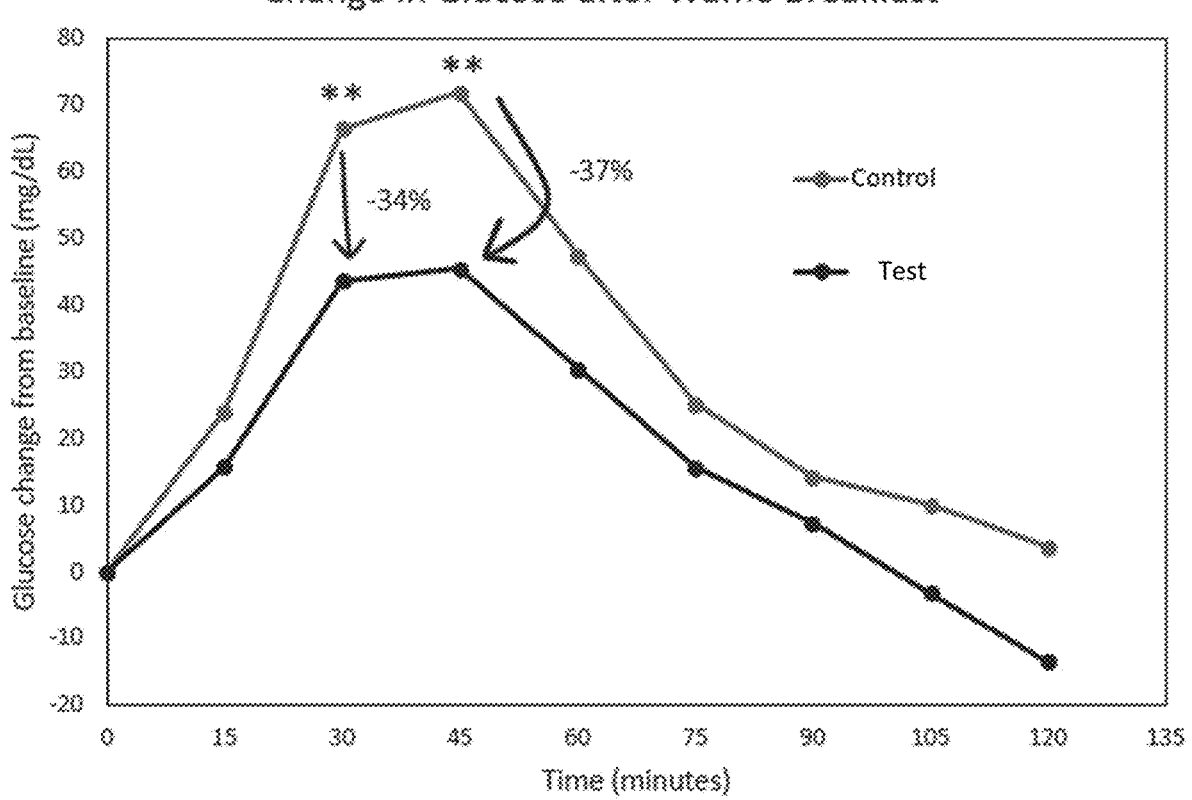

FIG. 11 illustrates a line graph depicting an embodiment of comparisons of change in glucose after a waffle breakfast in subjects who ingest the fiber supplement on one occasion or control (no pre-meal fiber) on another occasion.

Figure 12:
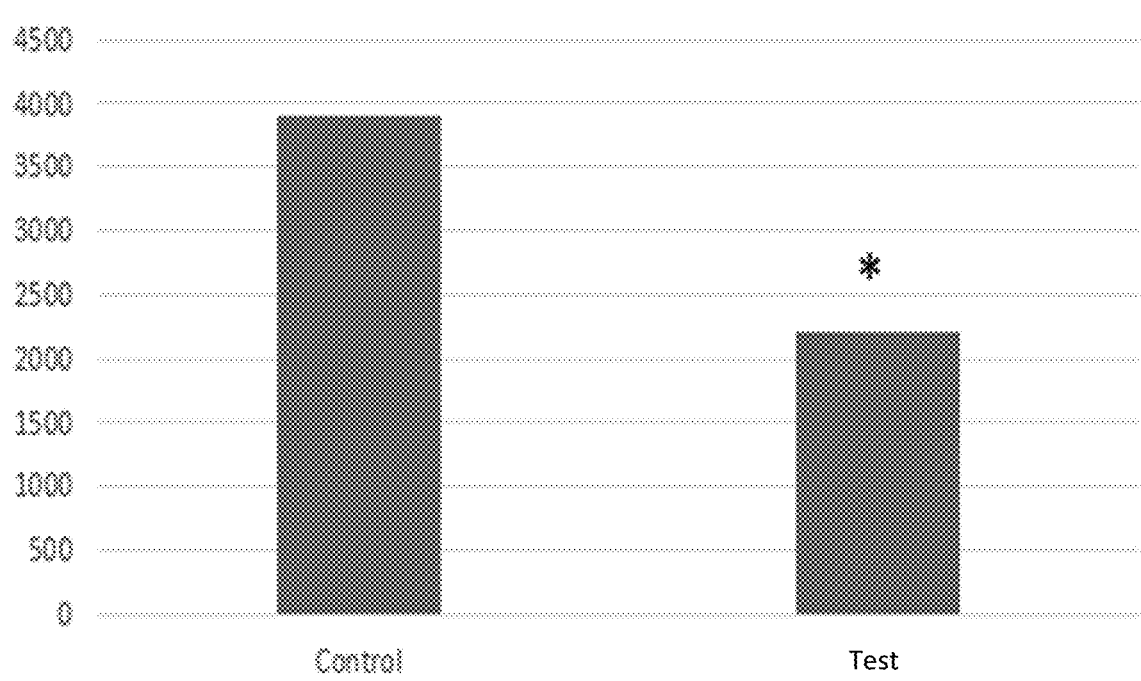

FIG. 12 is a bar graph depicting an embodiment of changes in post-meal 2-hour glucose between subjects who ingested a fiber supplement on one occasion or control (no pre-meal fiber) on another occasion.

DETAILED DESCRIPTION

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented herein. It will be readily understood that the aspects of the present disclosure, as generally described herein, and illustrated in the drawings, can be arranged, substituted, combined, separated, and designed in a wide variety of different configurations, all of which are explicitly contemplated herein.

As summarized herein, aspects of product combinations, methods, kits, and compositions for improving health and well-being using a yerba mate supplement and a fiber supplement are provided herein.

It is to be understood that this disclosure is not limited to particular embodiments described, as such may, of course, vary. It is also to be understood that the terminology used herein is for the purpose of describing particular embodiments only, and is not intended to be limiting.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Unless defined otherwise, technical and scientific terms used herein have the same meaning as commonly understood by one of ordinary skill in the art to which the present disclosure belongs.

All publications, patent applications, patents, and other references mentioned herein are incorporated by reference in their entirety. In case of conflict, the present specification, including explanations of terms, will control. In addition, the materials, methods, and examples are illustrative only and not intended to be limiting.

In some embodiments, provided herein are product combinations, methods, kits, and compositions for improving health and well-being using a yerba mate supplement and a fiber supplement. In some embodiments, methods of treating a patient include ingesting a yerba mate supplement after waking, fasting for a 12-18 hour fasting interval, and ingesting a fiber supplement before meal consumption.

Advantageously, the product combinations, methods, kits, and compositions described herein help bridge the gap between a subject's current health and a subject's health goals. The product combinations, methods, kits, and compositions described herein make a healthy lifestyle possible and enjoyable for a subject. The product combinations, methods, kits, and compositions described herein take out guesswork, stress, and excessive meal preparation for a subject. The product combinations, methods, kits, and compositions described herein help a subject feel fuller for longer, prolong breaks between meals, and give the subject's body the nutrients that it needs. Advantageously, the methods, compositions, and kits result in improved health and well-being, which include, for example, improved blood lipid levels, reduced body weight, reduced fasting blood sugar levels, increased feelings of positive experiences, and decreased feelings of negative experiences.

In some embodiments, methods described herein combine approaches of yerba mate supplements, fiber supplements, and a time-based eating patterns.

Yerba Mate Supplement

In some embodiments, the methods include ingesting a yerba mate supplement. In some embodiments, the yerba mate supplement is administered or ingested. In some embodiments, the yerba mate supplement is ingested at the beginning of the day. In some embodiments, the yerba mate supplement is ingested within one hour of waking. In some embodiments, the yerba mate supplement is ingested within two hours of waking. In some embodiments, the yerba mate supplement is ingested within three hours of waking. In some embodiments the yerba mate supplement is ingested within about fifteen minutes, about thirty minutes, about one hour, about two hours, about three hours, or about four hours of waking.

In some embodiments, the yerba mate supplement is ingested following or near the end of an 8-20 hour fasting period. In some embodiments, the yerba mate supplement is ingested following or near the end of a 12-16 hour fasting period. For example, the fasting period may be about 8, about 9, about 10 hours, about 11 hours, about 12 hours, about 13 hours, about 14 hours, about 15 hours, about 16 hours, about 17 hours, about 18 hours, about 19 hours, or about 20 hours. In some embodiments, the fasting period takes place over night.

In some embodiments, the yerba mate supplement is mixed with a liquid. The liquid can include any quantity of liquid, including, for example, an amount ranging from about 10 to about 1200 mL of liquid. In some embodiments, the yerba mate supplement is mixed with 500-700 mL of liquid. For example, the yerba mate supplement may be mixed with about 10, 20, 30, 40, 50, 60, 70, 80, 90, 100, 150, 200, 300, 400, 500, 600, 700, 800, 900, 1000, 1100, or 1200 mL of liquid, or an amount within a range defined by any two of the aforementioned values. In some embodiments, the liquid is water, tea, milk, seltzer, juice, nut milks, coffees, energy drinks, oat beverages, electrolyte solution, or other liquids.

Yerba mate has been traditionally used to promote mental clarity, endurance, appetite control, and an improved mood. In some embodiments, the yerba mate leaves in the yerba mate supplement have been prepared by handpicking, extracting, concentrating, and/or purifying. In some embodiments, the yerba mate supplement boosts the benefits of yerba mate and contains up to 10 times the amount of total chlorogenic acids (mood-enhancing, brain-stimulating, feel-good elements) found in a premium cup of coffee.

Yerba mate comes from a plant native to South America, where it has been consumed in community rituals for hundreds of years. Its unique blend of plant compounds—including chlorogenic acids, mate saponins, and theobromine—is known to improve mood, heighten mental clarity, and suppress the appetite.

In some embodiments, the yerba mate supplement includes at least 10% total chlorogenic acids, at least 0.1% theobromine, and 1-8% caffeine. In some embodiments, the yerba mate supplement includes at least 20% total chlorogenic acids, at least 0.3% theobromine, and 1-6% caffeine. In some embodiments, the yerba mate supplement includes about 5%, about 10%, about 15%, about 20%, about 25%, about 30%, about 35%, about 40%, about 45%, about 50%, about 55%, or about 60% total chlorogenic acids. In some embodiments, the yerba mate supplement includes about 0.1%, about 0.5%, about 1%, about 1.5%, about 2%, about 2.5%, about 3%, about 3.5%, about 4%, about 4.5%, about 5%, about about 6%, about 6.5%, about 7%, about 7.5%, about 8%, about 8.5%, about 9%, about 9.5%, about 10%, about 10.5%, about 11%, about 11.5%, about 12%, about 12.5%, about 13%, about 13.5%, about 14%, about 14.5%, about 15%, about 15.5%, about 16%, about 16.5%, about 17%, about 17.5%, about 18%, about 18.5%, about 19%, about 19.5%, or about 20% theobromine. In some embodiments, the yerba mate supplement includes about 1%, about 1.5%, about 2%, about 2.5%, about 3%, about 3.5%, about 4%, about 4.5%, about 5%, about about 6%, about 6.5%, about 7%, about 7.5%, about 8%, about 8.5%, about 9%, about 9.5%, about 10%, about 10.5%, about 11%, about 11.5%, about 12%, about 12.5%, about 13%, about 13.5%, about 14%, about 14.5%, about 15%, about 15.5%, about 16%, about 16.5%, about 17%, about 17.5%, about 18%, about 18.5%, about 19%, about 19.5%, or about 20% caffeine.

In some embodiments, the yerba mate supplement is formulated as a powder or a drink. In some embodiments, the yerba mate supplement is formulated for oral ingestion. In some embodiments, the yerba mate supplement is formulated for topical application.

In some embodiments, the yerba mate supplement includes about 400 mg to about 800 mg of total chlorogenic acids. In some embodiments, the yerba mate supplement includes about 600 mg to about 1000 mg of total chlorogenic acids. In some embodiments, the yerba mate supplement includes about 800 mg to about 1200 mg of total chlorogenic acids. In some embodiments, the yerba mate supplement includes about 400 mg, about 500 mg, about 600 mg, about 700 mg, about 800 mg, about 900 mg, about 1000 mg, about 1100 mg, or about 1200 mg of total chlorogenic acids.

In some embodiments, the yerba mate supplement includes about 6 mg to about 17 mg of theobromine. In some embodiments, the yerba mate supplement includes about 9 mg to about 20 mg of theobromine. In some embodiments, the yerba mate supplement includes about 12 mg to about 23 mg of theobromine. In some embodiments, the yerba mate supplement includes about 5 mg, about 6 mg, about 7 mg, about 8 mg, about 9 mg, about 10 mg, about 11 mg, about 12 mg, about 13 mg, about 14 mg, about 15 mg, about 16 mg, about 17 mg, about 18 mg, about 19 mg, about 20 mg, about 21 mg, about 22 mg, about 23 mg, about 24 mg, about 25 mg, about 26 mg, about 27 mg, about 28 mg, about 29 mg, or about 30 mg of theobromine.

In some embodiments, the yerba mate supplement includes about 30 mg to about 150 mg caffeine. In some embodiments, the yerba mate supplement includes about 60 mg to about 180 mg caffeine. In some embodiments, the yerba mate supplement includes about mg to about 210 mg caffeine. In some embodiments, the yerba mate supplement includes about 20 mg, about 30 mg, about 40 mg, about 50 mg, about 60 mg, about 70 mg, about 80 mg, about 90 mg, about 100 mg, about 110 mg, about 120 mg, about 130 mg, about 140 mg, about 150 mg, about 160 mg, about 170 mg, about 180 mg, about 190 mg, about 200 mg, about 210 mg, about 220 mg, about 230 mg, about 240 mg, about 250 mg, about 260 mg, or about 270 mg caffeine.

In some embodiments, the yerba mate supplement includes about 600 mg of total chlorogenic acids, about 9 mg of theobromine, and about 120 mg of caffeine.

As used herein, the term "yerba mate" has its ordinary meaning as understood in light of the specification, and refers to the medicinal plant, *Ilex paraguariensis*.

In some embodiments, the yerba mate supplement is ingested once daily. In some embodiments, the yerba mate supplement is ingested twice daily, three times per day, or four times per day. In some embodiments, the yerba mate supplement is ingested every other day, once weekly, or twice weekly.

In some embodiments, the yerba mate supplement is prepared with hot liquid, such as hot water. In some embodiments, the hot water has a temperature from 50-100° C. In some embodiments, the yerba mate supplement is prepared with cold liquid, such as cold water. In some embodiments, the cold water has a temperature from 0-30° C. In some embodiments, the yerba mate supplement is prepared in combination with cinnamon, coconut cream, ice, sparkling water, lemon, ginger, citrus, mint, and/or protein powder or protein beverage.

In some embodiments, the yerba mate supplement is provided in bulk from which the quantity can be obtained and added to the liquid. In some embodiments, the yerba mate supplement is provided in single serving packaging. In some embodiments, the whole quantity in the packaging is added to the liquid. In some embodiments, partial quantity in the packaging is added to the liquid. In some embodiments, one packet of yerba mate supplement includes about 2 g to about 10 g of yerba mate supplement. For example, one packet of yerba mate supplement can include about 1 g, about 2 g, about 3 g, about 4 g, about 5 g, about 6 g, about 6.1 g, about 7 g, about 7.25 g, about 8 g, about 9 g, about 10 g, about 11 g, or about 12 g of yerba mate supplement. In some embodiments, about 10 packets to about 50 packets of yerba mate supplement are packaged together. For example, about 5 packets, about 10 packets, about 15 packets, about 20 packets, about 25 packets, about 30 packets, about 35 packets, about packets, about 45 packets, about 50 packets, about 55 packets, about 60 packets, about 65 packets, about 70 packets, about 75 packets, or about 80 packets of yerba mate supplement can be packaged together.

In some embodiments, the yerba mate supplement has greater than or equal to 20% caffeoylquinic acids. In some embodiments, the yerba mate supplement has 1-8% caffeine. In some embodiments, the yerba mate supplement has 1-6% caffeine. In some embodiments, the yerba mate supplement has greater than or equal to 0.3% theobromine. In some embodiments, the yerba mate supplement has at least 600 mg of total chlorogenic acids. In some embodiments, the yerba mate supplement has at least 9 mg of theobromine. In some embodiments, the yerba mate supplement has 60-180 mg of caffeine.

Fiber Supplement

In some embodiments, the methods include ingesting a fiber supplement before meal consumption. In some embodiments, the fiber supplement is ingested before each of two meals in a day. In some embodiments, the fiber supplement is ingested before one meal each day. In some embodiments, the fiber supplement is ingested before each of three meals in a day. In some embodiments, the fiber supplement is ingested before each of four meals in a day. In some embodiments, the fiber supplement is ingested after meal consumption, including after one meal a day, two meals a day, three meals a day, or four meals a day. In some embodiments the fiber supplement includes about 2 to about 10 g soluble fiber. For example, the fiber supplement may include about 1 g, about 2 g, about 3 g, about 4 g, about 5 g, about 6 g, about 7 g, about 8 g, about 9 g, or about 10 g soluble fiber. In some embodiments the fiber supplement includes about 100 to about 1200 mg phytosterols. In some embodiments the fiber supplement includes 250-1000 mg phytosterols. For example, the fiber supplement may include about 100 mg, about 200 mg, about 300 mg, about 400 mg, about 500 mg, about 600 mg, about 700 mg, about 800 mg, about 900 mg, about 1000 mg, about 1100 mg, or about 1200 mg phytosterols. In some embodiments, the fiber supplement is mixed with a liquid. In some embodiments, the liquid is an amount of about 10 to about 1200 mL, such as 10, 20, 30, 50, 60, 70, 80, 90, 100, 150, 200, 250, 300, 400, 500, 600, 700, 800, 900, 1000, 1100, or 1200 mL, or any amount within a range defined by any two of the aforementioned values. In some embodiments, the liquid is water, tea, milk, seltzer, juice, nut milks, coffees, energy drinks, oat beverages, electrolyte solution, or other liquids.

In some embodiments, the fiber supplement includes at least 50 mg polyphenol blend. For example, the fiber supplement can include about 50 mg, about 75 mg, about 100 mg, about 125 mg, about 150 mg, about 175 mg, about 200 mg, about 225 mg, about 250 mg, about 275 mg, about 300 mg, about 325 mg, about 350 mg, about 375 mg, about 400 mg, about 425 mg, about 450 mg, about 475 mg, about 500 mg, about 525 mg, about 550 mg, about 575 mg, about 600 mg, about 700 mg, about 800 mg, about 900 mg, or about 1000 mg polyphenol blend. In some embodiments, the polyphenol blend can include pomegranate extract, red grape extract, apple extract, or whole yeast fermentate. In some embodiments, the fiber supplement includes at least 5 mg of short-chain fructo-oligosaccharides. For example, the fiber supplement can include about 5 mg, about 6 mg, about 7 mg, about 8 mg, about 9 mg, about 10 mg, about 11 mg, about 12 mg, about 13 mg, about 14 mg, about 15 mg, about 16 mg, about 17 mg, about 18 mg, about 19 mg, about 20 mg, about 21 mg, about 22 mg, about 23 mg, about 24 mg, about 25 mg, about 26, about 27 mg, about 28 mg, about 29 mg, about mg, about 31 mg, about 32 mg, about 33 mg, about 34 mg, about 35 mg, about 36 mg, about 37 mg, about 38 mg, about 39 mg, about 40 mg, about 50 mg, about 60 mg, about 70 mg, about mg, about 90 mg, or about 100 mg of short-chain fructo-oligosaccharides.

In some embodiments, the fiber supplement is provided in bulk from which the quantity can be obtained and added to the liquid. In some embodiments, the fiber supplement is provided in single serving packaging. In some embodiments, the whole quantity in the packaging is added to the liquid. In some embodiments, partial quantity in the packaging is added to the liquid. In some embodiments, one packet of fiber supplement includes about 2 g to about 10 g of fiber supplement. For example, one packet of fiber supplement can include about 1 g, about 2 g, about 3 g, about 4 g, about 5 g, about 6 g, about 6.1 g, about 7 g, about 7.25 g, about 8 g, about 9 g, about 10 g, about 11 g, or about 12 g of fiber supplement. In some embodiments, about 10 packets to about 50 packets of fiber supplement are packaged together. For example, about 5 packets, about 10 packets, about 15 packets, about 20 packets, about 25 packets, about 30 packets, about 35 packets, about 40 packets, about 45 packets, about 50 packets, about 55 packets, about 60 packets, about 65 packets, about 70 packets, about 75 packets, or about 80 packets of fiber supplement can be packaged together.

In some embodiments, the fiber supplement is a pre-meal drink with a fiber matrix. In some embodiments, the fiber matrix includes bioactive plant compounds, polysaccharides, and micronutrients. In some embodiments, the fiber matrix is designed to help ease some of the impact that excess carbohydrates and cholesterol can have on the body. In some embodiments, the fiber supplement is formulated to provide critical vitamins, minerals, and soluble fibers to help curb a subject's appetite.

In some embodiments, the fiber supplement contains soluble fibers. In some embodiments, the fiber supplement is a blend of five types of soluble fibers. In some embodiments, the fiber supplements include guar gum, locust bean gum, citrus pectin, oat fiber, beta-glucans, and/or gum arabic. In some embodiments, the fiber supplement comprises at least one, at least two, at least three, at least four, at least five, or at least six of guar gum, locust bean gum, citrus pectin, oat fiber, beta-glucans, and/or gum arabic. In some embodiments, the fiber supplement includes a blend of plant-derived polysaccharides. In some embodiments, the fiber supplement includes a blend of plant extracts and phytosterols. In some embodiments, the fiber supplements include chrysanthemum extract and/or policosanol. In some embodiments the fiber supplement includes calcium carbonate, vitamin c (ascorbic acid), chromium, vitamin A (beta-carotene) vitamin E (D-alpha tocopheryl acetate), niacin (niacinaminde), zinc (zinc gluconate), vitamin B6 (pyridoxine HCl), vitamin B12 (cyanocobalamin), folic acid, vitamin B1 (thiamin HCl), biotin, and/or vitamin b12. In some embodiments, the fiber supplement includes vitamin A, vitamin C, vitamin E, thiamin, riboflavin, niacinamide, pyridoxine HCl, folic acid, cyanocobalamin, biotin, calcium carbonate, zinc gluconate, and/chromium, a polyphenol blend, magnesium oxide, pantothenic acid, or short-chain fructo-oligosaccharides.

In some embodiments, viscous, soluble fibers form a thick gel when mixed with water and as they move through the digestive tract. Without being bound to theory, the gel-like substance helps slow the emptying of the stomach, which results in prolonged satiety. In some embodiments, the fiber supplement is an excellent source of nine essential vitamins and minerals, including vitamin C and vitamin B12. Without being bound to theory, the vitamins and minerals promote proper digestion, optimize the conversion of food to fuel, and support healthy metabolism.

In some embodiments, the fiber supplement is ingested 1-20 minutes before the subject's two largest meals of the day. For example, the fiber supplement may be ingested about 1 minute, about 2 minutes, about 3 minutes, about 4 minutes, about 5 minutes, about 6 minutes, about 7 minutes, about 8 minutes, about 9 minutes, about 10 minutes, about 11 minutes, about 12 minutes, about 13 minutes, about 14 minutes, about 15 minutes, about 16 minutes, about 17 minutes, about 18 minutes, about 19 minutes, or about 20 minutes before a subject's meal, or an amount of time within a range defined by any two of the aforementioned values. In some embodiments, the fiber supplement is ingested immediately before a subject's meal. In some embodiments, the fiber supplement is ingested immediately before the subject's two largest meals of the day. In some embodiments, a packet of fiber supplement is mixed with liquid in a shaker cup. In some embodiments, the fiber supplement is ingested immediately after mixing with liquid.

In some embodiments, the fiber supplement may be ingested in combination with a protein powder, an energy powder, and/or a flavored water or low-calorie drink.

In some embodiments, the fiber supplement and the yerba mate supplement are provided as a product combination, where the separate formulations are provided together to a subject, for ingestion, as detailed herein.

The yerba mate supplement and the fiber supplement of the product combinations, methods, kits, and compositions described herein may work together to help a subject extend the time between dinner and the first meal of the following day. Time-based eating, often referred to as intermittent fasting, has been associated with numerous health benefits, such as healthy blood pressure, improved heart health, and improved body composition. In some embodiments, the yerba mate supplement and the fiber supplement provide a synergistic effect when ingested separately. In some embodiments, the yerba mate supplement is ingested in the morning. In some embodiments, the fiber supplement is ingested before meals. In some embodiments, the yerba mate supplement and the fiber supplement are packaged separately.

In some embodiments, the subject can create a record of meal consumption. In some embodiments, a record of meal consumption is created for the user. In some embodiments, the record of meal consumption is a physical record. In some embodiments, the record of meal consumption is a digital record. In some embodiments, the record of meal consumption is logged on a computer. In some embodiments, the record of meal consumption is logged on a digital application, for example on a smart device. In some embodiments, the subject can create a record of the fasting interval. In some embodiments, a record of the fasting interval is created for the user. In some embodiments, the record of the fasting interval is a physical record. In some embodiments, the record of the fasting interval is a digital record. In some embodiments, the record of the fasting interval is logged on a computer. In some embodiments, the record of the fasting interval is logged on a digital application. In some embodiments, recording allows a user to track health progression, such as improvement toward well-being, weight goal, energy goal, or other health goals being tracked.

In some embodiments, the subject can create a record of ingestion of the yerba mate supplement. In some embodiments, a record of ingestion of the yerba mate supplement is created for the user. In some embodiments, the record of ingestion of the yerba mate supplement is a physical record. In some embodiments, the record of ingestion of the yerba mate supplement is a digital record. In some embodiments, the record of ingestion of the yerba mate supplement is logged on a computer. In some embodiments, the record of ingestion of the yerba mate supplement is logged in an application. In some embodiments, the subject can create a record of ingestion of the fiber supplement. In some embodiments, a record of ingestion of the fiber supplement is created for the user. In some embodiments, the record of ingestion of the fiber supplement is a physical record. In some embodiments, the record of ingestion of the fiber supplement is a digital record. In some embodiments, the record of ingestion of the fiber supplement is logged on a computer. In some embodiments, the record of ingestion of the fiber supplement is logged in an application.

Intermittent Fasting

In some embodiments, the product combinations, kits, and compositions disclosed herein are used in combination with fasting. Further, some embodiments provided herein relate to methods of improving health and well-being by combining the compositions provided herein with fasting. In some embodiments, fasting includes fasting for a period of time ranging from about 8 to about 20 hours, such as 8, 9, 10, 11, 12, 13, 14, 15, 16, 17, 18, 19, or 20 hours, or a time frame within a range defined by any two of the aforementioned values.

Insulin is the hormone that is responsible for moving glucose, or sugar, from the blood into the cells for energy. Without being bound by theory, when a subject consumes carbohydrates, blood sugar levels rise, and insulin is released. In some diets, a subject has a steady supply of carbohydrates triggering this glucose-insulin response. When the body is in a constant cycle of high blood sugar and high insulin levels, it can become insulin resistant. Over time, this can wreak havoc on the body's systems. If a subject stops constantly eating, then the subject's body has the time it needs to go into a natural fat-burning state instead of relying on a steady supply of glucose.

In some embodiments, to keep insulin levels in check, the spacing between a subject's meals can be increased. The less a subject's insulin spikes, the more time the subject may spend in the fat-fueled state instead of the carb-fueled state. Intermittent fasting may include time-based eating that can help the body maintain healthy insulin levels.

In some embodiments, following a fasting period as described herein, such as a fasting period ranging from about 8-20 hours, a subject takes one or more meals, such as a first meal, a second meal, and/or a third meal. In some embodiments, a gap is included between meals, such as a gap ranging from 2-6 hours, such as 2, 2.5, 3, 3.5, 4, 4.5, 5, 5.5, or 6 hour gaps between meals, or an amount within a range defined by any two of the aforementioned values. In some embodiments, there is a 4-hour gap between the second and third meals of the day. In some embodiments, fasting for a period of about 8 to about 20 hours begin from the last meal of one day until the first meal of the next day.

Some embodiments provided herein are described as set forth in the following enumerated alternatives.

1. A product combination for improving health and well-being in a subject, comprising: a yerba mate supplement comprising at least 20% total chlorogenic acids, at least 0.3% theobromine, and 1-6% caffeine; and a fiber supplement comprising at least 3.5 g soluble fiber and 250-1000 mg phytosterols.

2. The product combination of alternative 1, wherein the soluble fiber comprises guar gum, locust bean gum, citrus pectin, oat fiber, beta-glucans, or gum arabic.

3. The product combination of any one of alternatives 1-2, wherein the fiber supplement further comprises vitamin A, vitamin C, vitamin E, thiamin, riboflavin, niacinamide, pyridoxine HCl, folic acid, cyanocobalamin, biotin, calcium carbonate, zinc gluconate, chromium, a polyphenol blend, magnesium oxide, pantothenic acid, or short-chain fructo-oligosaccharides.

4. The product combination of any one of alternatives 1-3, wherein the yerba mate supplement is formulated as a powder or a drink.

5. The product combination of any one of alternatives 1-4, wherein the fiber supplement is formulated as a powder or a drink.

6. The product combination of any one of alternatives 1-5, wherein the yerba mate supplement and the fiber supplement are formulated for oral ingestion.

7. The product combination of any one of alternatives 1-6, wherein the yerba mate supplement and the fiber supplement are packaged separately.

8. The product combination of any one of alternatives 1-7, wherein the yerba mate supplement and the fiber supplement are formulated for ingestion at different time intervals.

9. The product combination of any one of alternatives 1-8, wherein the yerba mate supplement and the fiber supplement provide a synergistic effect when ingested separately.

10. The product combination of any one of alternatives 1-9, wherein the yerba mate supplement is formulated for ingestion at least once daily.

11. The product combination of any one of alternatives 1-10, wherein the fiber supplement is formulated for ingestion at least twice daily.

12. The product combination of any one of alternatives 1-11, wherein the yerba mate supplement comprises at least 600 mg of total chlorogenic acids.

13. The product combination of any one of alternatives 1-12, wherein the yerba mate supplement comprises about 9 mg to about 20 mg of theobromine.

14. The product combination of any one of alternatives 1-13, wherein the yerba mate supplement comprises about 60 mg to about 180 mg caffeine.

15. The product combination of any one of alternatives 1-14, wherein the yerba mate supplement comprises about 600 mg of total chlorogenic acids, about 9 mg of theobromine, and about 120 mg of caffeine.

16. A method for improving health and well-being in a subject, comprising: fasting for a fasting interval; ingesting a yerba mate supplement during the fasting interval; and ingesting a fiber supplement following the fasting interval.

17. The method of alternative 16, wherein the fasting interval comprises 12-18 hours.

18. The method of any one of alternatives 16-17, wherein the yerba mate supplement comprises at least 600 mg of total chlorogenic acids.

19. The method of any one of alternatives 16-18, wherein the yerba mate supplement comprises at least 9 mg of theobromine.

20. The method of any one of alternatives 16-19, wherein the yerba mate supplement comprises 60-180 mg of caffeine.

21. The method of any one of alternatives 16-20, further comprising mixing the fiber supplement with liquid.

22. The method of any one of alternatives 16-21, further comprising mixing the yerba mate supplement with liquid.

23. The method of any one of alternatives 21-22, wherein the liquid is water.

24. The method of any one of alternatives 21-23, wherein the liquid is tea.

25. The method of any one of alternatives 21-24, wherein the liquid is an electrolyte solution.

26. The method of any one of alternatives 21-25, wherein the liquid is in an amount of at least 240 mL.

27. The method of any one of alternatives 21-26, wherein the liquid is in an amount ranging from about 400 mL to about 800 mL.

28. The method of any one of alternatives 16-27, wherein the fiber supplement is ingested 10-20 minutes prior to a first meal.

29. The method of any one of alternatives 16-28, further comprising ingesting the fiber supplement 10-20 minutes prior to a second meal.

30. A kit comprising: a first composition comprising a yerba mate supplement comprising at least 600 mg total chlorogenic acids, at least 9 mg theobromine, and 60-180 mg caffeine; a second composition comprising a fiber supplement comprising at least 3.5 g soluble fiber and 250-1000 mg phytosterols; and a third composition comprising a fiber supplement comprising at least 3.5 g soluble fiber and 250-1000 mg phytosterols.

31. The kit of alternative 30, wherein the soluble fiber comprises guar gum, locust bean gum, citrus pectin, oat fiber, beta-glucans, or gum arabic.

32. The kit of any one of alternatives 30-31, wherein the fiber supplement further comprises vitamin A, vitamin C, vitamin E, thiamin, riboflavin, niacinamide, pyridoxine HCl, folic acid, cyanocobalamin, biotin, calcium carbonate, zinc gluconate, chromium, a polyphenol blend, magnesium oxide, pantothenic acid, or short-chain fructo-oligo saccharide s.

33. The kit of any one of alternatives 30-32, wherein the yerba mate supplement is formulated as a powder or a drink.

34. The kit of any one of alternatives 30-33, wherein the fiber supplement is formulated as a powder or a drink.

35. The kit of any one of alternatives 30-34, wherein the yerba mate supplement and the fiber supplement are formulated for oral ingestion.

36. The kit of any one of alternatives 30-35, wherein the yerba mate supplement and the fiber supplement are packaged separately within the kit.

37. The kit of any one of alternatives 30-36, wherein the yerba mate supplement and the fiber supplement are formulated for ingestion at different time intervals.

38. The kit of any one of alternatives 30-37, wherein the yerba mate supplement and the fiber supplement have a synergistic effect when ingested separately.

39. The kit of any one of alternatives 30-38, wherein the yerba mate supplement is formulated for ingestion at least once daily.

40. The kit of any one of alternatives 30-39, wherein the fiber supplement is formulated for ingestion at least twice daily.

41. The kit of any one of alternatives 30-40, wherein the yerba mate supplement comprises at least 600 mg of total chlorogenic acids.

42. The kit of any one of alternatives 30-41, wherein the yerba mate supplement comprises at least 9 mg of theobromine.

43. The kit of any one of alternatives 30-42, wherein the yerba mate supplement comprises 60-180 mg caffeine.

44. The kit of any one of alternatives 30-43, further comprising an electronic system to track intake of the yerba mate supplement or the fiber supplement.

45. The kit of any one of alternatives 30-44, further comprising an electronic system to track a fasting interval.

46. A composition for use in improving health and well-being, wherein the composition is for ingestion, the composition comprising: a yerba mate supplement comprising at least 20% total chlorogenic acids, at least 0.3% theobromine, and 1-6% caffeine; and a fiber supplement comprising at least 3.5 g soluble fiber and 250-1000 mg phytosterols.

47. The composition of alternative 46, wherein the soluble fiber comprises guar gum, locust bean gum, citrus pectin, oat fiber, beta-glucans, or gum arabic.

48. The composition of any one of alternatives 46-47, wherein the fiber supplement further comprises vitamin A, vitamin C, vitamin E, thiamin, riboflavin, niacinamide, pyridoxine HCl, folic acid, cyanocobalamin, biotin, calcium carbonate, zinc gluconate, chromium, a polyphenol blend, magnesium oxide, pantothenic acid, or short-chain fructo-oligosaccharides.

49. The composition of any one of alternatives 46-48, wherein the yerba mate supplement is formulated as a powder or a drink.

50. The composition of any one of alternatives 46-49, wherein the fiber supplement is formulated as a powder or a drink.

51. The composition of any one of alternatives 46-50, wherein the yerba mate supplement and the fiber supplement are formulated for oral ingestion.

52. The composition of any one of alternatives 46-51, wherein the yerba mate supplement and the fiber supplement are packaged separately.

53. The composition of any one of alternatives 46-52, wherein the yerba mate supplement and the fiber supplement are formulated for ingestion at different time intervals.

54. The composition of any one of alternatives 46-53, wherein the yerba mate supplement and the fiber supplement provide a synergistic effect when ingested separately.

55. The composition of any one of alternatives 46-54, wherein the yerba mate supplement is formulated for ingestion at least once daily.

56. The composition of any one of alternatives 46-55, wherein the fiber supplement is formulated for ingestion at least twice daily.

57. The composition of any one of alternatives 46-56, wherein the yerba mate supplement comprises at least 600 mg of total chlorogenic acids.

58. The composition of any one of alternatives 46-57, wherein the yerba mate supplement comprises at least 9 mg of theobromine.

59. The composition of any one of alternatives 46-58, wherein the yerba mate supplement comprises at least 60 mg caffeine.

60. The composition of any one of alternatives 46-59, wherein the yerba mate supplement comprises about 600 mg of total chlorogenic acids, about 9 mg of theobromine, and about 120 mg of caffeine.

61. The composition of any one of alternatives 46-60, wherein improving health and well-being comprises improving blood lipid levels, reducing body weight, reducing fasting blood sugar levels, increasing feelings of positive experiences, or decreasing feelings of negative experiences.

EXAMPLES

Example 1

Summary: This study was conducted to measure changes in cardiometabolic health among participants following a daily supplementation protocol for 60 days. During the trial, participants experienced significant improvements in important markers of metabolic health, including blood lipids, triglycerides, and glycated hemoglobin (HbA1c) levels, as well as decreases in body weight and waist circumference.

Background: The following study was conducted to measure cardiometabolic changes among participants following treatment with a method including daily supplementation and time-restricted eating protocol for 60 days. The daily protocol consists of following a time-restricted eating approach (eating window 8-10 hours) and dietary supplementation with yerba mate supplement and fiber supplement that, in combination, provide fiber and polyphenolic compounds with numerous benefits for cardiometabolic health (Anderson, Nutr Rev, 2009; Lutomski, Ann Agric Environ Med, 2020; Gambero, Nutrients, 2015).

Methods: This was an open-label interventional study of 42 healthy participants, ages 20-65 years, and who followed a program using methods described herein for 60 days. The program consisted of two supplements to consume daily as indicated: 1) a powdered yerba mate drink mix, consumed once in the morning during the "fasting" period (N=42), and 2) a fiber supplement, consumed twice per day (N=34) 15 minutes prior to a meal. A small group of participants (N=8) were assigned to take only one serving of the fiber supplement per day to determine the effects, if any, of product dose on study outcomes. In addition, participants fasted overnight for 14-16 hours throughout the 60 days.

The yerba mate supplement contained naturally occurring chlorogenic acids, caffeine and theobromine (methylxanthines), and triterpene saponins. The fiber supplement contained 4 g of fiber from a variety of sources along with minerals, vitamins, policosanol, phytosterols, and *Chrysanthemum morifolium* extract.

Measurements collected at Days 0 (baseline), 30 and 60 included anthropometry (weight and waist circumference), and blood lipid levels (cholesterol profile and triglycerides) and percent hemoglobin A1c (% HbA1c) were assessed at Day 0 and Day 60.

Results: Repeated measures ANOVA revealed significant decreases in weight and waist circumference (p=0.0008 and p=0.0045) among all study participants over the three time-points (FIG. 1). Furthermore, paired tests revealed significant decreases in non-high-density lipoprotein (non-HDL), low-density lipoprotein (LDL), and total cholesterol (FIG. 2). Triglycerides and percent hemoglobin A1C (% HbA1c) were also significantly lower among all participants after 60 days (FIG. 2). A significant increase (p=0.0085) was observed in % HDL cholesterol after 60 days (FIG. 3). Slight improvements in plasma biomarkers were seen among participants consuming two daily servings of fiber supplement compared to one, but these differences were not statistically significant (data not shown). Subjects were stratified by high versus low baseline non-HDL cholesterol (non-HDL-c, >145 mg/dL or ≤145 mg/dL). Those in the high non-HDL-c group (N=24) displayed a significant improvement over 60 days in non-HDL-c, LDL-c, total cholesterol, and % HbA1c, while subjects in the low baseline non-HDL-c group (N=18) did not (FIG. 4). No significant changes were observed in HDL-c, triglycerides, or % HDL.

FIG. 1 depicts percent change in body weight and waist circumference of participants from baseline (Day 0) to Day 30 and Day 60. Mean body weight and waist circumference of participants significantly decreased by 1.1% and 2.0%, respectively, after 60 days of yerba mate supplement in combination with fiber supplement. Dunnett's multiple comparisons: *p<0.05, **p<0.01.

FIG. 2 depicts percent change from baseline to Day 60 in lipid and glucose biomarkers. Total, non-HDL and LDL cholesterol, triglycerides, and % HbA1c all significantly decreased by 5.7%, 7.4%, 7.6%, 9.0%, and 1.3%, respectively. Paired t-test: *p<0.05; Wilcoxon signed rank test: p<0.05.

FIG. 3 depicts percent change from baseline to Day 60 in HDL cholesterol and % HDL. Percent HDL cholesterol significantly increased by 10% after 60 days on the yerba mate supplement in combination with fiber supplement system. Paired t-test: **p<0.01.

FIG. 4 depicts stratification of participants with Low vs High baseline non-HDL cholesterol. (Low: ≤145 mg/dL, High: >145 mg/dL). Significant improvements from day 0 to 60 were only detected in the High baseline group. 2-way repeated measures ANOVA: *p<0.05, **p<0.01.

Conclusion: Results suggest the program can help improve important markers of cardiovascular and metabolic health. In particular, the program can help improve total, non-HDL, and LDL cholesterol, as well as % HbA1c, in those with higher levels of non-HDL cholesterol. More research is needed to understand the effect of varying fiber supplement dosages on those with normal and abnormal lipid and glucose metabolism.

Example 2

FIG. 5 illustrates a line graph depicting lower desire to eat after consuming a yerba mate supplement.

Summary: Acute appetite and satiety response to a yerba mate supplement was measured among a group of participants following a 12-hour overnight fast. In this exploratory study, participants reported lower desire to eat at 15, 30, and 45 minutes following yerba mate supplement consumption (*p<0.05, **p<0.01) compared to baseline (0 min). However, due to the small sample size, some differences from the placebo arm were not statistically significant for other appetite outcomes. These preliminary results suggest that the yerba mate supplement may have an appetite-suppressing effect, and further research is warranted.

Background: The yerba mate supplement is a dietary supplement drink mix that contains chlorogenic acids, methylxanthines, triterpene saponins, and other bioactive phytocompounds from the yerba mate plant, *Ilex paraguariensis*. Traditionally, this herbal tea has been thought to have a multitude of effects, including boosting energy and feelings of well-being while promoting satiety and reducing appetite (Lutomski, Ann Agric Environ Med, 2020; Gambero, Nutrients, 2015). Previous work has suggested that yerba mate tea may regulate appetite through delaying gastric emptying or through upregulation of glucagon-like peptide 1 and leptin (Hussein, Biol Pharm Bull, 2011; Andersen, J Hum Nutr Diet, 2001). Novel nutritional products that can help manage weight or modulate appetite are especially relevant, as the World Health Organization has estimated that more than 1.9 billion adults are either overweight or obese. Thus, this preliminary study was conducted to evaluate the acute appetite response following yerba mate supplement consumption.

Methods: This was a single-blind, exploratory study with 26 healthy adults (ages 20-65 years). A subgroup of these subjects (N=9) also completed a blinded placebo arm with a lemon-flavored beverage mix on a separate day. In the morning, while fasted, subjects consumed one serving of yerba mate supplement or Placebo in 500 ml water. Subjective ratings for appetite (hunger, fullness, desire to eat, and prospective consumption) were recorded with a visual analog scale (VAS) prior to (0 min) and after 15, 30, 45, 60, 90 and 120 minutes of consumption. An area under the curve (AUC) was derived for each individual scale item plotted over measured time points.

Results: FIG. 6 panels A-D show the response curves for select VAS items. While trends suggest increased appetite suppression after consuming yerba mate supplement, AUCs were not statistically different between the test (N=26) and placebo groups (N=9). Relative to baseline (0 min) responses, subjects appeared to have lower desire to eat and feeling of hunger than in the placebo arm. Participants also reported a greater feeling of fullness and felt like they could eat less than they could in the placebo condition.

FIG. 6 depicts VAS subjective ratings of 'desire to eat' (A), 'feeling of hunger' (B), 'feeling of fullness' (C), and 'prospective consumption' (D) over 120 minutes following consumption of yerba mate supplement (N=26) versus Placebo (N=9). Ratings were normalized relative to Baseline (0 min).

FIG. 7 shows the overall AUC for select VAS items, suggesting lower appetite after consuming the test product among the nine participants who completed both arms. Paired tests did not reveal statistical differences between the AUC of the placebo and test groups. However, pairwise comparisons of 'desire to eat' at 15, 30, and 45 minutes post-consumption were significantly different from baseline (0 min) after consuming yerba mate supplement (FIG. 5). FIG. 5 shows within-subject comparisons (N=9) of 'desire to eat' over 120 minutes following consumption of yerba mate supplement versus Placebo. (2-way ANOVA, Dunnett's multiple comparisons test; *p<0.05 and **p<0.01 relative to baseline).

Conclusion: These preliminary data suggest short-term appetite suppression may be experienced following consumption of yerba mate supplement. Further study with a larger subject group in a randomized, double-blind, placebo-controlled trial is warranted.

Example 3

FIG. 8 illustrates a bar graph depicting improvements in well-being after 30 and 60 days of treatment with a method described herein.

Summary: This study measured changes in well-being among participants following a daily supplementation protocol. Participants' Affect Balance scores on the Scale of Positive and Negative Experiences (SPANE) were significantly higher after 30 and 60 days of following the yerba mate supplement in combination with fiber supplement system (p<0.0001 and p<0.001, respectively), suggesting improved well-being.

Background: The following study was conducted to measure changes in feelings of well-being among participants following treatment with a method, which consists of daily supplementation with yerba mate supplement and fiber supplement. In combination, these two products provide fiber, polyphenols and other beneficial compounds shown to enhance both physical and cognitive health and performance (Andersen, Nutr Rev, 2009; Lutomski, Ann Agric Environ Med, 2020; Gambero, Nutrients, 2015). The yerba mate supplement is a yerba mate-based dietary supplement containing chlorogenic acids, methylxanthines, and triterpene saponins that may support feelings of well-being and happiness (Gawron-Gzella, Nutrients, 2021).

Methods: This was an open-label interventional study. Participants were 37 healthy adults (ages 20-65 years) who received treatment for 60 days. The protocol consisted of two supplements to consume as indicated: 1) a yerba mate-based supplement, consumed once in the morning, and 2) a fiber supplement, consumed twice per day 15 minutes prior to a meal. In addition, participants fasted overnight for 12-16 hours, throughout the 60 days. A subset of participants (N=7) were assigned to take only one serving of fiber supplement per day to determine the effects, if any, of dose on study outcomes. Subjects in this group still consumed one serving of fiber supplement per day and fasted overnight for 12-16 hours.

On Days 0 (Baseline), 30, and 60, the 12-item Scale of Positive and Negative Experiences (SPANE) was administered. This is a validated survey tool for assessing well-being in which frequency of experiencing Positive Feelings (positive, good, pleasant, happy, joyful, and contented) and frequency of experiencing Negative Feelings (negative, bad, unpleasant, sad, afraid, and angry) over a 4-week timespan are reported retrospectively by the subject (Diener, Soc Int Res, 2010). The SPANE Affect Balance is determined by subtracting the sum total of Negative Feelings from the sum total of Positive Feelings.

Results: The Affect Balance is an overall measure of happiness or well-being, and scores may range from the unhappiest possible (−24) to the highest balance possible (24). Repeated measures ANOVA indicated significant increases on the Affect Balance SPANE Score. As shown in FIG. 9, pairwise comparisons to Day 0 revealed a highly significant increase in overall well-being after 30 and 60 days of the protocol (p<0.0001 and p=0.0003, respectively).

The two components of the Affect Balance are the Positive Feelings score and Negative Feelings score. Positive Feelings scores increased significantly from baseline after 30 days (p=0.02) and 60 days (p=0.008), indicating greater frequency of experiencing positive feelings. In contrast, Negative Feelings scores decreased significantly from baseline after 30 days (p<0.0001) and 60 days (p=0.0001), suggesting fewer experiences of negative feelings. No differences were seen between participants consuming one or two doses of fiber supplement per day (data not shown).

FIG. 9 depicts affect Balance SPANE score (overall happiness) at Days 30 & 60 significantly increased from Day 0 (Dunnett's multiple comparisons vs. Day 0: p<0.001, p<0.0001).

FIG. 10 depicts positive Feelings score at Days 30 & 60 significantly increased 16% and 18%, respectively, from Day 0. Negative Feelings score at Days 30 & 60 significantly decreased by 20% and 18%, respectively, from Day 0. (Dunnett's multiple comparisons: *p<0.05, **p<0.01, p<0.001, p<0.0001.)

Conclusion: Treatment with methods described herein may lead to improved quality of life. Overall happiness and well-being significantly increased after 30 and 60 days on the program, as measured by the validated SPANE assessment. Larger trials are needed to confirm any impact on the effect of varying supplement dosage on well-being. The methods' other potential benefits include improved cardiovascular and metabolic health.

Example 4

Summary: In the following example, a study was conducted to measure changes in the glucose response to a typical breakfast meal with and without pre-meal fiber supplement consumption in generally healthy adults. Continuous glucose monitor (CGM) readings showed a lower peak glucose spike and lower overall 2-hour post-meal glucose response (area under the curve) to the same meal when fiber supplement was consumed 15 minutes before eating compared to the Control (no fiber supplement) condition.

Methods: This was an open-label, randomized, interventional study of nine healthy participants (Ages 28-56 years, 56% female). Participants wore a continuous glucose monitor (CGM) throughout the study, and CGM output for two hours following the test meals was evaluated to determine the post-prandial glucose response. The test meal consisted of two waffles, 30 g syrup, and 10 oz. (296 mL) orange juice, with 89 g total carbohydrates (Table 1). No food, except water, was consumed before the morning test meal. On separate testing days, participants either drank one serving of fiber supplement in 8 oz. water 15 minutes prior to the test meal, or nothing for the control condition. After 15 minutes, the test meal was consumed. No other food was eaten for 2.5 hours following breakfast. Meal times and physical activity were controlled and consistent between treatments.

Table 1 describes the nutritional composition of the breakfast test meal consisting of two waffles, 30 g syrup, and 10 oz. orange juice.

TABLE 1

| Total Calories | 420 calories |
|---|---|
| Total Carbohydrates | 89 g |
| Total Sugars | 51 g |
| Dietary Fiber | 1 g |

Results: A two-way repeated measures ANOVA revealed significant treatment (P=0.03) and time (P<0.0001) effects. Compared to Control, pre-meal supplementation with fiber supplement significantly reduced glucose levels 30 and 45 minutes after eating by 34% and 37%, respectively (P<0.01, FIG. 11). The 2-hour area under the curve (AUC), which represents the overall glucose response to the meal, was also significantly lower after taking fiber supplement (P=0.019, FIG. 12). Finally, maximal change in glucose from baseline was suppressed with fiber supplement compared to Control (mean±SD: 52±15 mg/dL vs. 78±13 mg/dL; paired t-test, one-tailed: p=0.004).

FIG. 11 illustrates a line graph depicting comparisons of change in glucose after a waffle breakfast in subjects who ingest the fiber supplement versus a control. Advantageously, the fiber supplement significantly lowers the post-prandial glucose response to a high carbohydrate meal in subjects.

FIG. 12 illustrates a bar graph illustrating that post-meal 2-hour glucose AUC was 43% lower with fiber supplement (n=9). Asterisks are used to denote significant different with a paired t-test, one-tailed p-value: p=0.019.

Considerations: In an acute study with nine healthy adults, pre-meal supplementation with fiber supplement lowered the glucose response to a typical breakfast meal. This suggests that taking fiber supplement prior to a high carbohydrate meal can reduce the impact of dietary carbohydrates in the body, potentially due to a reduction in post-prandial glucose load.

Example 5

Summary: The following study was conducted to determine the sub-chronic effect (4-day intervention, 3 of which were included in the analysis) of a system that combines yerba mate extract supplement, fiber supplement, and intermittent fasting, on glycemic variability and glycemic control in men and women with risk factors for impaired fasting glucose.

Fiber supplement: A dietary fiber supplement in powder form included guar gum, phytosterols, blend of plant derived polysaccharides, orange flavor, gum arabic, locust bean gum, maltodextrin, citrus pectin, oat fiber, orange juice powder, citric acid, calcium carbonate, vitamin C, chromium yeast, vitamin A, sucralose, beta-glucan, vitamin E, niacin, zinc, chrysanthemum (flower) extract, vitamin B6, policosanol, vitamin B12, folic acid, vitamin B1, biotin, and vitamin B2.

Yerba mate supplement (lemon flavored): A powdered supplement included green yerba mate leaf extract with sweeteners and flavor added.

Methods: This was a single-blind, single-arm study that included one screening visit, one baseline phase, two intervention phases, and one follow-up visit. A continuous glucose monitor was applied and activated for each eligible participant at Visit 2.

Subjects (n=50) were adults aged ≥30 to ≤69 years old with body mass index (BMI) ≥25.0 to <35.0 kg/m2 and meeting at least 1 out of 3 of the following criteria: waist circumference >102 cm for men and >88 cm for women, family history of at least one parent or sibling with diagnosed impaired fasting glucose (IFG) or type 2 diabetes mellitus (T2DM), and/or sedentary lifestyle (based on self-report). Subjects also met all other inclusion criteria, and did not meet any exclusion criteria.

During the baseline phase, subjects were instructed to maintain their habitual diet. During Phase 1, subjects took a yerba mate supplement once a day and a fiber supplement twice per day for 4 days. During Phase 2, subjects followed the yerba mate supplement in combination with fiber supplement system including yerba mate supplement and fiber supplement with 16:8 (16-hour fast, 8-hour eating period) intermittent fasting for 4 days. Participants were asked to complete an electronic daily diary and a Gastrointestinal Tolerability Questionnaire (GITQ).

Results: The improvement in overall glycemic variability appears to be driven by a shift in the amount of time glucose values were within the ideal range of 70-140 mg/dL (89.6% to 94.0%) with corresponding reductions in average time spent in the hypoglycemic range <70 mg/dL (4.3% to 1.9%) and hyperglycemic range >140 mg/dL (6.1% to 4.1%). These shifts were also evident during the daytime hours, except for the >140 md/dL range. Change in CV from baseline to Phase 2 was not significant during daytime only hours (secondary outcome). There were no differences in mean glucose nor the odds of experiencing at least one hypoglycemic event.

Other secondary outcomes included the supplementation only period (Phase 1). Glycemic variability and mean glucose, relative to the baseline habitual diet period were not different when analyzed as 2 weekdays and 1 weekend day per period (per the SAP). However, the percent of time glucose was in the ideal range (70-140 mg/dL) increased from a mean of 89.6% to 93.2%, driven by a decrease (4.3% to 2.2%) in the percent of time glucose values were <70 mg/dL (not significant for >140 mg/dL). These results were consistent over all study days (sensitivity analysis) and when analyzed during only daytime hours (excluding midnight to 5:59 am). The odds of experiencing at least one hypoglycemic event were lower following the supplementation regimen compared to the baseline habitual diet period.

The articles "a" and "an" are used herein to refer to one or to more than one (to at least one) of the grammatical object of the article. By way of example, "an element" means one element or more than one element.

By "about" is meant a quantity, level, value, number, frequency, percentage, dimension, size, amount, weight or length that varies by as much as 30, 25, 20, 15, 10, 9, 8, 7, 6, 5, 4, 3, 2 or 1% to a reference quantity, level, value, number, frequency, percentage, dimension, size, amount, weight or length.

Throughout this specification, unless the context requires otherwise, the words "comprise," "comprises," and "comprising" will be understood to imply the inclusion of a stated step or element or group of steps or elements but not the exclusion of any other step or element or group of steps or elements.

By "consisting of" is meant including, and limited to, whatever follows the phrase "consisting of" Thus, the phrase "consisting of" indicates that the listed elements are required or mandatory, and that no other elements may be present. By "consisting essentially of" is meant including any elements listed after the phrase and limited to other elements that do not interfere with or contribute to the activity or action specified in the disclosure for the listed elements. Thus, the phrase "consisting essentially of" indicates that the listed elements are required or mandatory, but that other elements are optional and may or may not be present depending upon whether or not they materially affect the activity or action of the listed elements.

REFERENCES

The following references are expressly incorporated herein by reference in their entireties for all purposes.

Andersen T, Fogh J. Weight loss and delayed gastric emptying following a South American herbal preparation in overweight patients. J Hum Nutr Diet. 2001 June; 14(3): 243-50.

Anderson J W, Baird P, Davis R H Jr, Ferreri S, Knudtson M, Koraym A, Waters V, Williams C L. Health benefits of dietary fiber. Nutr Rev. 2009 April; 67(4):188-205.

Bastos, D. H. M., De Oliveira, D. M., Matsumoto, R. L. T., Carvalho, P. de O., & Ribeiro, M. L. (2007). Yerba mate: pharmacological properties, research and biotechnology. Med Aromat Plant Sci Biotechnol, 1(1), 37-46.

Bojić, M., Simon Haas, V., Šarić, D., & Maleš, Ž. (2013). Determination of flavonoids, phenolic acids, and xanthines in mate tea (Ilex paraguariensis St.-Hil.). Journal of Analytical Methods in Chemistry, 2013.

Burris, K. P., Harte, F. M., Davidson, P. M., Stewart Jr, C. N., & Zivanovic, S. (2012). Composition and bioactive properties of yerba mate (Ilex paraguariensis A. St.-Hil.): a review. Chilean Journal of Agricultural Research, 72(2), 268.

Chandrasekara, A., & Shahidi, F. (2018). Herbal beverages: Bioactive compounds and their role in disease risk reduction-A review. Journal of Traditional and Complementary Medicine, 8(4), 451-458.

Chianese, G., Golin-Pacheco, S. D., Taglialatela-Scafati, O., Collado, J. A., Munoz, E., Appendino, G., & Pollastro, F. (2019). Bioactive triterpenoids from the caffeine-rich plants guayusa and maté. Food Research International, 115, 504-510.

Croge, C. P., Cuquel, F. L., & Pintro, P. T. M. (2020). Yerba mate: cultivation systems, processing and chemical composition. A review. Scientia Agricola, 78(5).

Diener E, Wirtz D, Tov W, Kim-Prieto C, Choi D, Oishi S, Biswas-Diener R. New measures of well-being: Flourishing and positive and negative feelings. Social Indicators Research. 2010 Jan. 1; 39:247-266.

Ferreira Cuelho, C. H., de França Bonilha, I., Scotti do Canto, G., & Palermo Manfron, M. (2015). Recent advances in the bioactive properties of yerba mate. Revista Cubana de Farmacia, 49(2), 375-383.

Frizon, C. N. T., Perussello, C. A., Sturion, J. A., & Hoff-mann-Ribani, R. (2018). Novel Beverages of Yerba-Mate and Soy: Bioactive Compounds and Functional Proper-ties. Beverages, 4(1), 21.

Gambero A, Ribeiro M L. The positive effects of yerba maté (*Ilex paraguariensis*) in obesity. Nutrients. 2015 Jan. 22; 7(2):730-50.

Gawron-Gzella A, Chanaj-Kaczmarek J, Cielecka-Piontek J. Yerba Mate-A Long but Current History. Nutrients. 2021 Oct. 21; 13(11):3706.

Heck, C. I., & De Mejia, E. G. (2007). Yerba Mate Tea (*Ilex paraguariensis*): a comprehensive review on chemistry, health implications, and technological considerations. Journal of Food Science, 72(9), R138-R151.

Hussein G M, Matsuda H, Nakamura S, Hamao M, Akiyama T, Tamura K, Yoshikawa M. Mate tea (*Ilex paraguarien-sis*) promotes satiety and body weight lowering in mice: involvement of glucagon-like peptide-1. Biological & pharmaceutical bulletin. 2011; 34(12): 1849-1855.

Isolabella, S., Cogoi, L., López, P., Anesini, C., Ferraro, G., & Filip, R. (2010). Study of the bioactive compounds variation during yerba mate (*Ilex paraguariensis*) pro-cessing. Food Chemistry, 122(3), 695-699.

Junior, E. L. C., & Morand, C. (2016). Interest of mate (*Ilex paraguariensis* A. St.-Hil.) as a new natural functional food to preserve human cardiovascular health—A review. Journal of Functional Foods, 21, 440-454.

Lutomski P, Goździewska M, Florek-Łuszczki M. Health properties of Yerba Mate. Ann Agric Environ Med. 2020 Jun. 19; 27(2):310-313.

Matei, M. F., Jaiswal, R., Patras, M. A., & Kuhnert, N. (2016). LC-MSn study of the chemical transformations of hydroxycinnamates during yerba maté (*Ilex paraguarien-sis*) tea brewing. Food Research International, 90, 307-312.

Oellig, C., Schunck, J., & Schwack, W. (2018). Determina-tion of caffeine, theobromine and theophylline in Mate beer and Mate soft drinks by high-performance thin-layer chromatography. Journal of Chromatography A, 1533, 208-212.

Puangpraphant, S. (2012). Anti-inflammatory and anti-colon cancer potential of yerba mate (*Ilex paraguariensis* St. Hilaire) bioactive constituents. University of Illinois at Urbana-Champaign.

Riachi, L. G., Simas, D. L. R., Coelho, G. C., Marcellini, P. S., da Silva, A. J. R., & de Maria, C. A. B. (2018). Effect of light intensity and processing conditions on bioactive compounds in maté extracted from yerba mate (*Ilex paraguariensis* A. St.-Hil.). Food Chemistry, 266, 317-322.

Souza, A. H. P., Corrêa, R. C. G., Barros, L., Calhelha, R. C., Santos-Buelga, C., Peralta, R. M., Bracht, A., Matsushita, M., & Ferreira, I. C. F. R. (2015). Phytochemicals and bioactive properties of *Ilex paraguariensis*: An in-vitro comparative study between the whole plant, leaves and stems. Food Research International, 78, 286-294.

What is claimed is:

1. A composition for improving health or well-being, the composition comprising:

a yerba mate supplement comprising at least 20% total chlorogenic acids, at least 0.3% theobromine, and 1-6% caffeine, wherein the yerba mate supplement com-prises:

at least 600 mg total chlorogenic acids;
at least 9 mg theobromine; and
about 60-180 mg caffeine; and a fiber supplement comprising at least 3.5 g soluble fiber and 250-1000 mg phytosterols.

2. The composition of claim 1, wherein the soluble fiber comprises guar gum, locust bean gum, citrus pectin, oat fiber, beta-glucans, or gum arabic.

3. The composition of claim 1, wherein the fiber supple-ment further comprises vitamin A, vitamin C, vitamin E, thiamin, riboflavin, niacinamide, pyridoxine HCl, folic acid, cyanocobalamin, biotin, calcium carbonate, zinc gluconate, chromium, a polyphenol blend, magnesium oxide, pantoth-enic acid, or short-chain fructo-oligosaccharides.

4. The composition of claim 1, wherein the yerba mate supplement and the fiber supplement are formulated as a powder or a drink.

5. The composition of claim 1, wherein the yerba mate supplement and the fiber supplement are formulated for oral ingestion.

6. The composition of claim 1, wherein the yerba mate supplement and the fiber supplement are packaged sepa-rately.

7. The composition of claim 1, wherein the yerba mate supplement and the fiber supplement are formulated for ingestion at different time intervals.

8. The composition of claim 1, wherein the yerba mate supplement is formulated for ingestion at least once daily.

9. The composition of claim 1, wherein the fiber supple-ment is formulated for ingestion at least twice daily.

10. The composition of claim 1, wherein the yerba mate supplement comprises at least 60 mg caffeine.

11. The composition of claim 1, wherein the yerba mate supplement comprises about 600 mg of total chlorogenic acids, about 9 mg of theobromine, and about 120 mg of caffeine.

12. A method for improving health or well-being in a subject, comprising:

fasting for a fasting interval of about 12-18 hours;

ingesting a yerba mate supplement during the fasting interval;

ingesting a fiber supplement following the fasting inter-val; and wherein improving health or well-being comprises improving blood lipid levels, reducing body weight, reducing fasting blood sugar levels, increasing feelings of positive experiences, or decreasing feelings of nega-tive experiences.

13. The method of claim 12, wherein the yerba mate supplement comprises at least 600 mg of total chlorogenic acids.

14. The method of claim 12, wherein the yerba mate supplement comprises at least 9 mg of theobromine.

15. The method of claim 12, wherein the yerba mate supplement comprises 60-180 mg of caffeine.

16. The method of claim 12, further comprising mixing the fiber supplement or the yerba mate supplement with a liquid.

17. The method of claim 16, wherein the liquid is water.

18. The method of claim 16, wherein the liquid is tea.

19. The method of claim 16, wherein the liquid is an electrolyte solution.

20. The method of claim 16, wherein the liquid is in an amount ranging from about 200 mL to about 800 mL.

21. The method of claim 14, wherein the fiber supplement is ingested 10-20 minutes prior to a first meal and 10-20 minutes prior to a second meal.

\* \* \* \* \*